US007659081B2

(12) United States Patent
Cuttitta et al.

(10) Patent No.: US 7,659,081 B2
(45) Date of Patent: Feb. 9, 2010

(54) DETERMINATION OF AM-BINDING PROTEINS AND THE ASSOCIATION OF ADRENOMEDULLIN (AM) THEREWITH

(75) Inventors: Frank Cuttitta, Adamstown, MD (US); Ted H. Elsasser, Berwyn Heights, MD (US); Alfredo Martinez, McLean, VA (US); Rubén Pio, Pamplona (ES)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 12/236,418

(22) Filed: Sep. 23, 2008

(65) Prior Publication Data

US 2009/0053734 A1 Feb. 26, 2009

Related U.S. Application Data

(60) Division of application No. 11/530,411, filed on Sep. 8, 2006, now abandoned, which is a continuation of application No. 10/070,853, filed as application No. PCT/US00/24722 on Sep. 8, 2000, now abandoned.

(60) Provisional application No. 60/153,397, filed on Sep. 10, 1999.

(51) Int. Cl.
G01N 33/53 (2006.01)
(52) U.S. Cl. .................... 435/7.1; 436/86; 436/161; 436/501; 436/507; 436/518
(58) Field of Classification Search ............... None
See application file for complete search history.

(56) References Cited

U.S. PATENT DOCUMENTS

| 4,444,879 | A | * | 4/1984 | Foster et al. ............... 435/7.95 |
| 4,774,323 | A | | 9/1988 | Newman et al. |
| 4,883,784 | A | | 11/1989 | Kaneko |
| 5,641,685 | A | | 6/1997 | Anumula |

FOREIGN PATENT DOCUMENTS

| WO | WO 97/07214 | * | 2/1997 |
| WO | WO97 07214 A | | 2/1997 |

OTHER PUBLICATIONS

Kato et al. (Endocrinology, 1997, vol. 138, No. 6, pp. 2615-2620).*
Sato et al. (Life Sciences, vol. 57., No. 2, pp. 189-194, 1995).*
Martinez et al. (Endocrinology, vol. 138, No. 12, 1997, pp. 5597-5604).*
Congote, "Reversed-phase high pressure liquid chromatography of globin chains: its application for the prenatal diagnosis of beta-thalassemia." *Prog Clin Biol Res*. 60:39-52, 1981.
Elsasser et al., "Adrenomedullin Binding Protein in the Plasma of Multiple Species: Characterization by Radioligand Blotting," *Endocrinology*, 140(10):4908-4911, 1999.
Hatefi and Hanstein, "Solubilization of particulate proteins and nonelectrolytes by chaotropic agents," *Proc. Natl. Acad. Sci.*, 62(4):1129-36, 1969.
Kato et al., Adrenomedullin As An Autocrine/Paracrine Apoptosis Survival Factor For Rat Endothelial Cells, *Endocrinology*, 138(6): 2615-2620, 1997.
Martinez et al., "Adrenomedullin Binding Protein-1 (AMBP-1) Modulates Tumor Growth by Reducing Availability of Adrenomedullin (AM)," *Proceedings of the American Association for Cancer Research*, 41: 153, 2000.
Martinez et al., "Expression of Adrenomedullin and Its Receptor in Normal and Malignant Human Skin: A Potential Pluripotent Role in the Integument," *Endocrinology*, 138(12): 5597-5604, 1997.
Martinez et al., "Is Adrenomedullin A Causal Agent In Some Cases Of Type 2 Diabetes?," *Peptides*, 20: 1471-1478, 1999.
Martinez et al., "Regulation of Insulin Secretion and Blood Glucose Metabolism by Adrenomedullin," *Endocrinology*, 137(6): 2626-2632, 1996.
Opperman et al., "Quantitation of Components of the Alternative Pathway of Complement (APC) by Enzyme-linked Immunosorbent Assays," *J. Immunol. Methods.*, 133(2): 181-190, 1990 (abstract only).
Pio et al., "Detection of Adrenomedullin Binding Proteins in Human Plasma by a Novel Non-Radioactive Method," *1999 Summer Neuropeptide Conference (Ninth Annual)*, Jun. 27, 1999.
Pio et al., "Isolation and Characterization of a Human Plasma Adrenomedullin Binding Protein, Analysis of Its Expression in Human Tumor Cell Lines," *Proceedings of the American Association for Cancer Research*, 41: 152, 2000.
Sato et al., "Characterization Of Immunoreactive Adrenomedullin In Human Plasma And Urine," *Life Sciences*, 57(2): 189-194, 1995.
Tsang et al., "Optimum Dissociating Condition For Immunoaffinity And Preferential Isolation Of Antibodies With High Specific Activity," *Journal of Immunological Methods*, 138: 291-299, 1991.
Wikipedia, "chaotropic agent", http//en.wikipedia.org/wiki/Chaotropic_agent, dated Mar. 27, 2006.

\* cited by examiner

*Primary Examiner*—Lisa V Cook
(74) *Attorney, Agent, or Firm*—Klarquist Sparkman, LLP

(57) ABSTRACT

The present invention provides methods for the isolation, identification, and purification of adrenomedullin (AM)-binding proteins. Also, provided are methods for utilizing the purified AM-binding proteins, or functional portions thereof, to diagnose, treat, and monitor AM-related diseases, for example, diseases or disorders associated with abnormally elevated AM levels. In addition, the present invention provides a newly identified complex between AM and a specific AM-binding protein 1 (AMBP-1); which has been isolated and identified herein as factor H (fH). The invention also provides AM/AMBP complexes, particularly AM/FH complexes, and antibodies specifically reactive with this complexes. Further provided are methods for identifying and purifying complexes of AM and an AM binding protein using anti-AM/fH antibodies, and methods for treating conditions such as cancer or diabetes utilizing compositions comprising these antibodies. The present invention additionally provides methods for identifying antagonists agents that inhibit the function of AM, factor H, or the AM/factor H complex. The invention also provides methods for treating conditions such as cancer or diabetes using these antagonist agents.

8 Claims, 18 Drawing Sheets

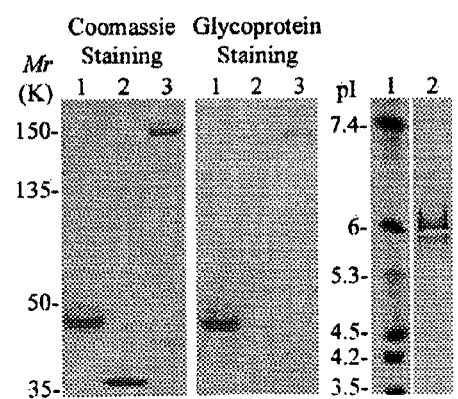
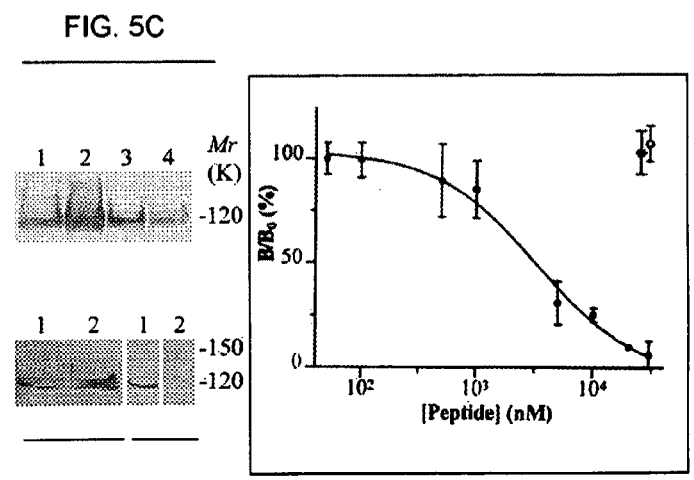
FIG. 5A  FIG. 5B  FIG. 5C  FIG. 5D  FIG. 5E  FIG. 5F

FIG. 6A
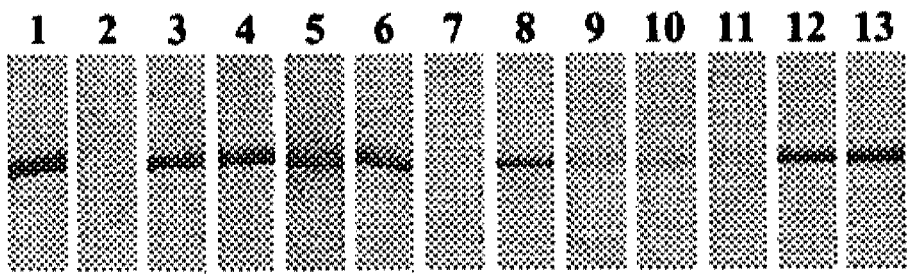
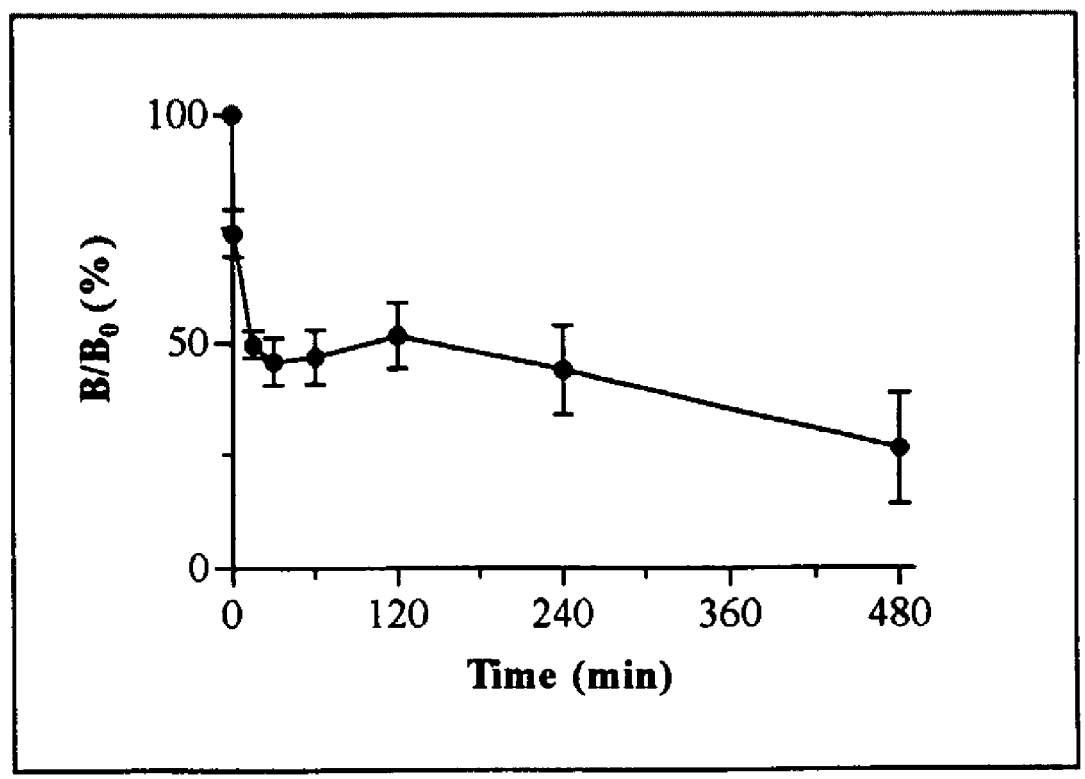
FIG. 6B

FIG. 7A
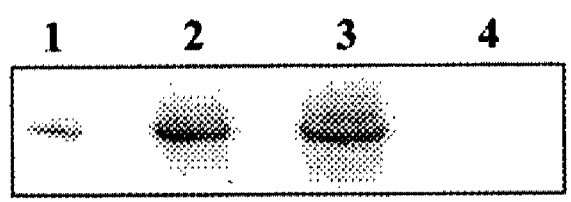
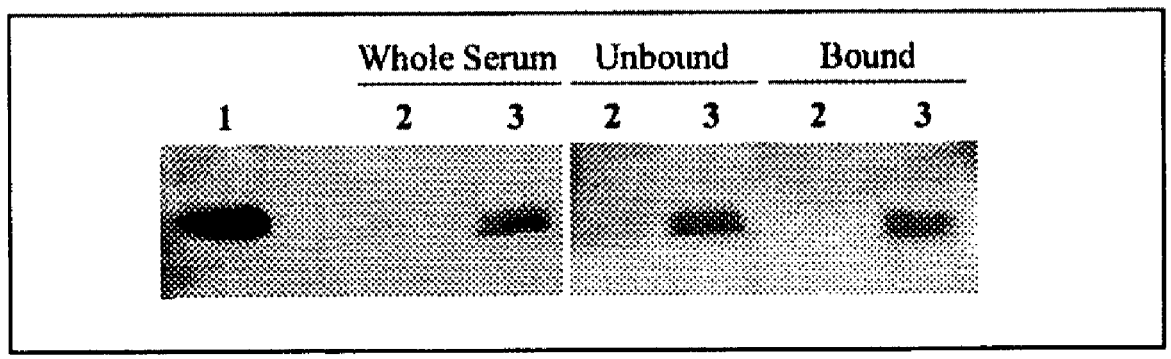
FIG. 7B

FIG. 10A
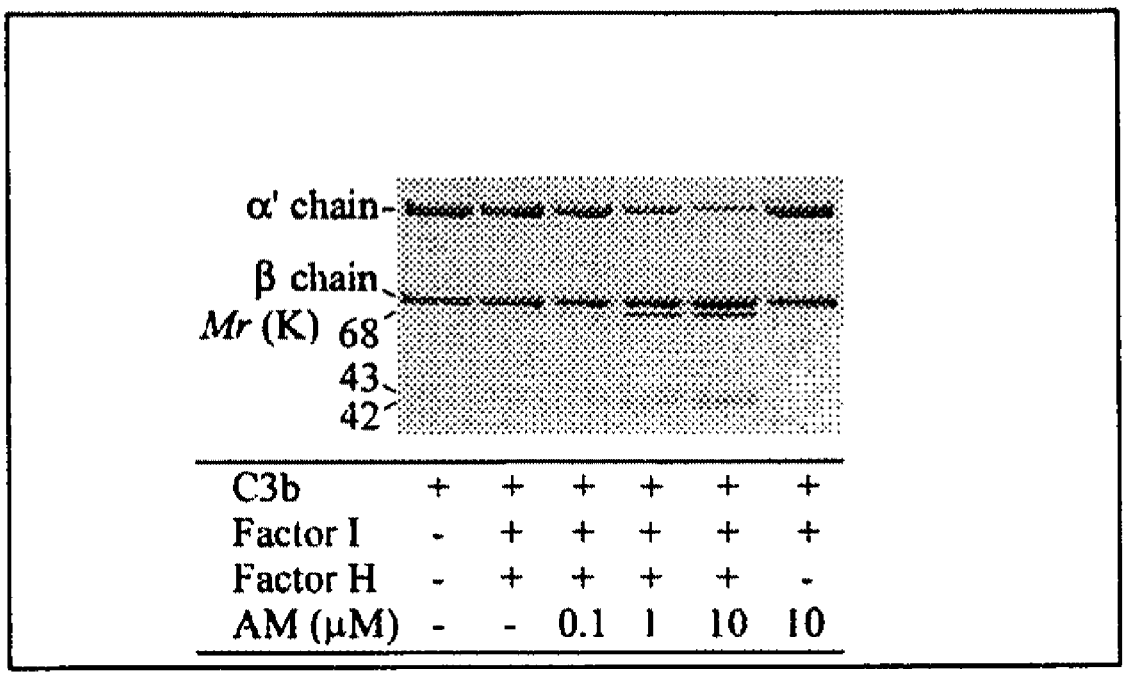
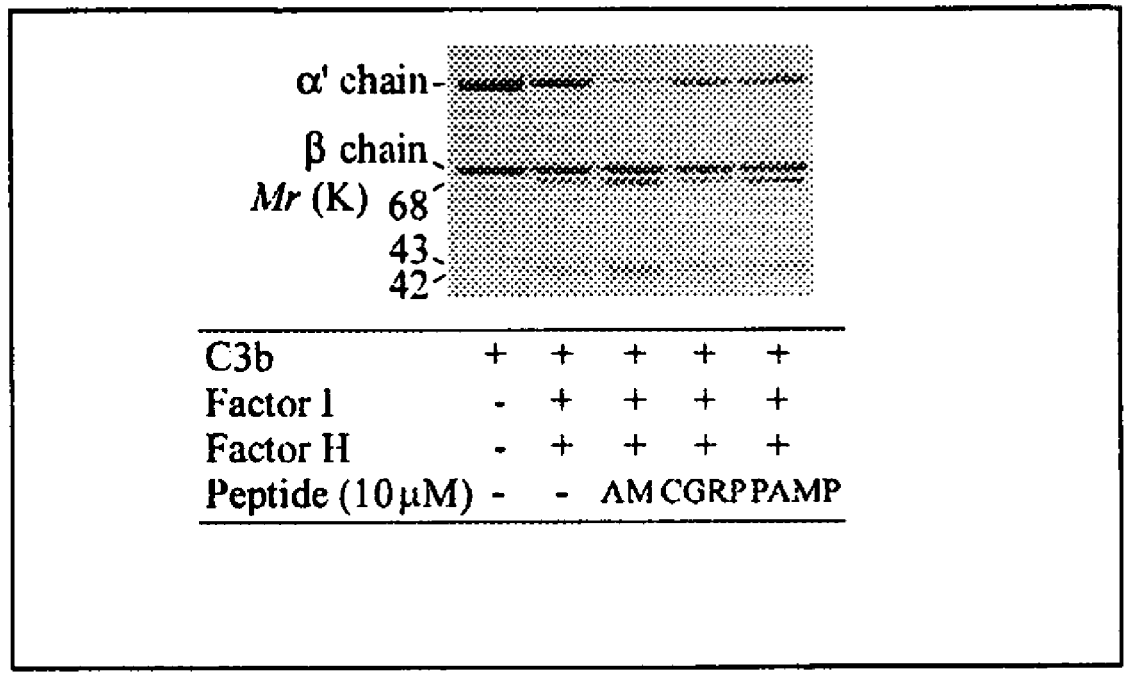
FIG. 10B

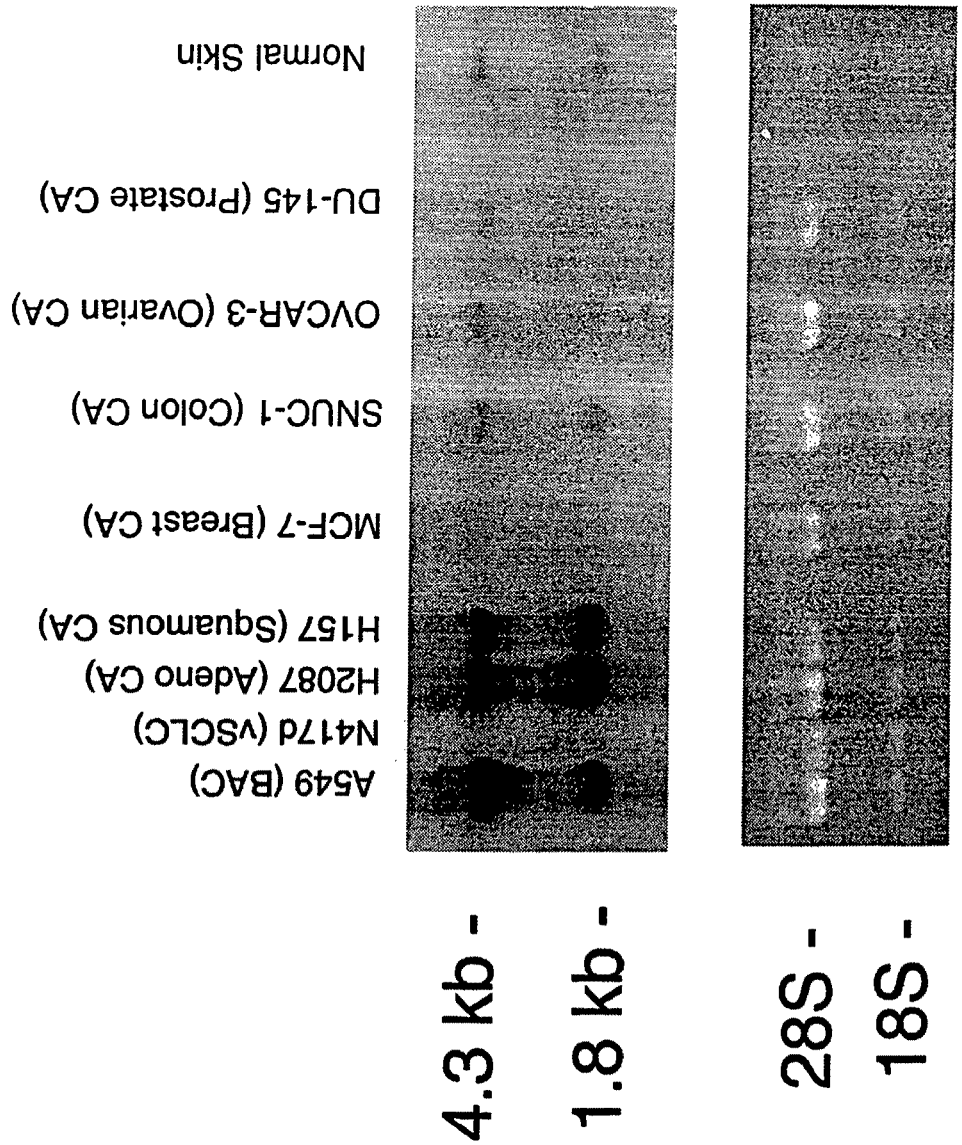

FIG. 12A     FIG. 12B     FIG. 12C
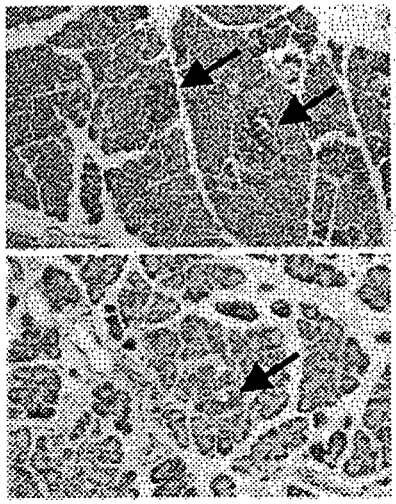 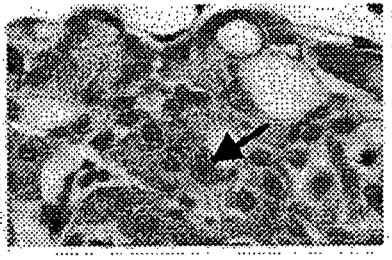 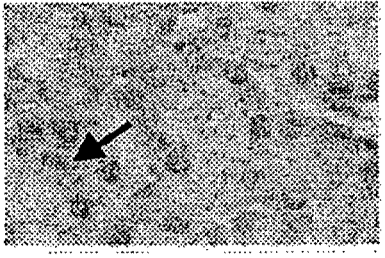
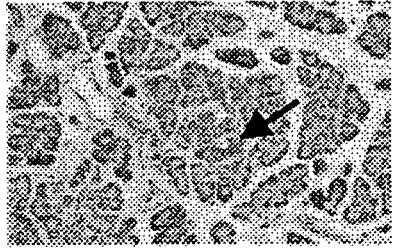
FIG. 12D

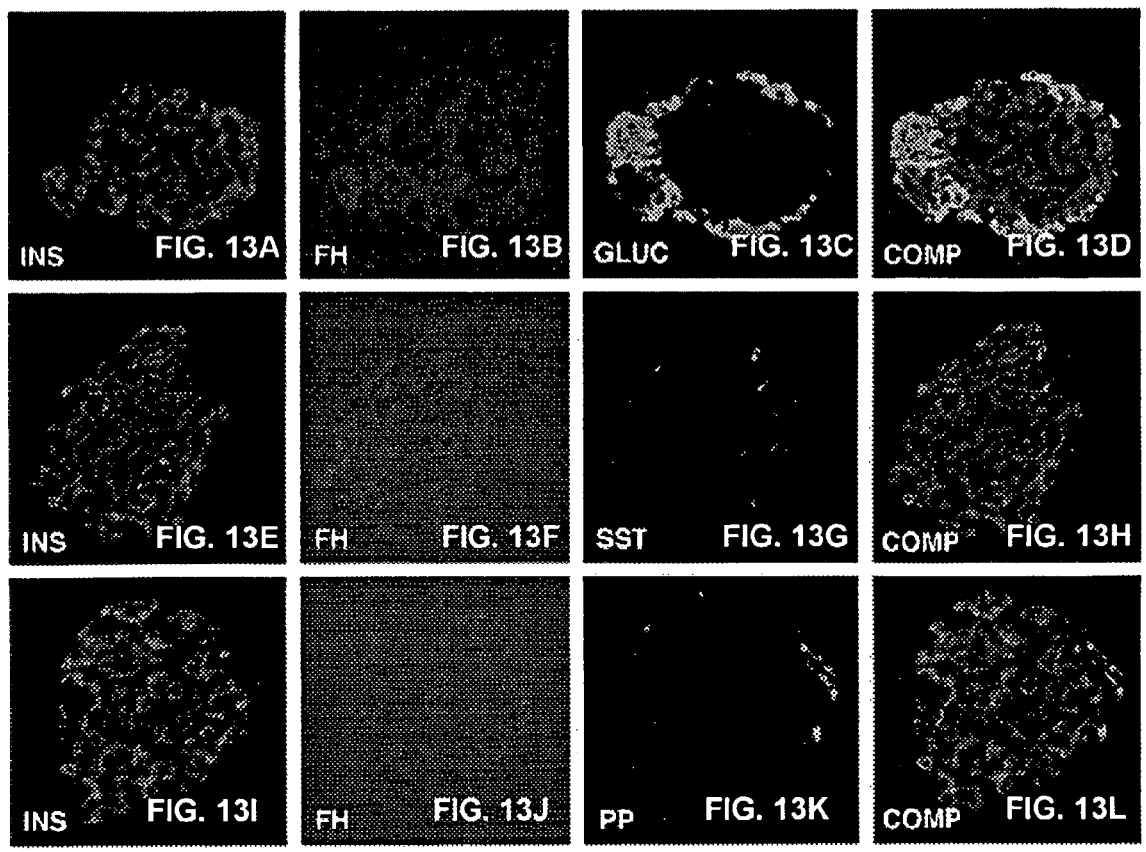

Eth. Br.

Southern

SEQUENCE LISTING

<160> NUMBER OF SEQ ID NOS: 4

<210> SEQ ID NO 1
<211> LENGTH: 22
<212> TYPE: DNA
<213> ORGANISM: artificial sequence
<220> FEATURE:
<223> OTHER INFORMATION: PCR Primer

<400> SEQUENCE: 1
caatggaacc agatcgggat ta                                                22

<210> SEQ ID NO 2
<211> LENGTH: 22
<212> TYPE: DNA
<213> ORGANISM: artificial sequence
<220> FEATURE:
<223> OTHER INFORMATION: PCR Primer

<400> SEQUENCE: 2
gacacggatg catctgggag ta                                                22

<210> SEQ ID NO 3
<211> LENGTH: 20
<212> TYPE: DNA
<213> ORGANISM: artificial sequence
<220> FEATURE:
<223> OTHER INFORMATION: PCR Primer

<400> SEQUENCE: 3
ttggaattct cctgccattc                                                   20

<210> SEQ ID NO 4
<211> LENGTH: 20
<212> TYPE: DNA
<213> ORGANISM: artificial sequence
<220> FEATURE:
<223> OTHER INFORMATION: PCR primer

<400> SEQUENCE: 4
accttccatc tttgcacacc                                                   20

DETERMINATION OF AM-BINDING PROTEINS AND THE ASSOCIATION OF ADRENOMEDULLIN (AM) THEREWITH

RELATED APPLICATION

This is a divisional of U.S. patent application Ser. No. 11/530,411, filed Sep. 8, 2006 now abandoned; which is a continuation of U.S. patent application Ser. No. 10/070,853, filed Aug. 26, 2002 (now abandoned); which is the §371 U.S. National Stage of PCT/US00/24722, filed Sep. 8, 2000, which was published in English under PCT Article 2(2); and which in turn claims the benefit of U.S. Provisional Application No. 60/153,397 filed Sep. 10 1999. These applications are incorporated herein in their entirety.

FIELD OF THE INVENTION

The present invention relates to newly developed methods for the detection of adrenomedullin (AM)-binding proteins. The invention further relates to the isolation, identification, and use of such AM-binding proteins, and to compositions and methods including these proteins. The AM-binding proteins can be employed in the diagnosis, treatment and monitoring of AM-related diseases. The present invention also relates to the isolation of AM/AM-binding protein complexes, the generation of antibodies to these complexes, and the use of these antibodies to detect AM/AM-binding protein complexes and treat AM-related diseases. The invention further relates to a newly discovered complex comprising AM and a newly identified AM binding protein, human complement factor H (fH; factor H). The present invention also relates to the identification of antagonists that dissociate the AM/fH complex or inhibit AM/fH complexation, and the use of such antagonists in the prevention and treatment of diseases, including cancers and diabetes.

BACKGROUND OF THE INVENTION

Adrenomedullin (AM) is a 52 amino acid amidated peptide hormone originally isolated from adrenal tumors. AM is involved in numerous physiological activities, including vasodilation, angiogenesis, mitogenesis, and anti-microbial functions. As a result, AM actions are related to a wide array of disease states such as heart and pulmonary disease, cirrhosis, cancer, diabetes, sepsis, inflammation and preeclampsia in mammals, including humans. (See, European Patent No. 0 845 036 and U.S. Ser. No. 09/011,922, filed Feb. 17, 1998 to F. Cuttitta et al.).

In clinical studies, patients with chronic congestive heart failure show elevated plasma AM, and these concentrations increase in proportion to the severity of the heart failure along with other hormones known to affect the progression of the disease (J. Kato et al., 1996, *J. Clin. Endocrinol. Metab.* 81:180-3). Similarly, patients with congenital cyanotic heart disease show elevated plasma AM levels and increased AM uptake in pulmonary circulation (M. Yoshibayashi et al, 1999, *Clin. Sci. (Colch.)*, 1999, 96:543-7). Patients with chronic obstructed pulmonary disease also show significantly raised AM plasma levels (B. Cheung et al., 1997, *Clin. Sci. (Colch.)* 92:59-62). Accordingly, increased AM (a potent vasodilator) may function as a compensatory mechanism for hypoxaemia (Kato et al., 1996, supra; Yoshibayashi et al., 1999, supra).

Several independent clinical studies have established that patients with liver cirrhosis show elevated circulating AM, and these levels increase with the severity of the illness (E. Fabrega et al., 1997, *Am. J. Gastroenterol.* 92:1901-4; C. M. Fernandez-Rodriguez et al., 1998, *J. Hepatol.* 29:250-6; M. Guevara et al., 1998, *Gastroenterology* 114:336-43; H Kojima et al., 1998, *J. Hepatol.* 28:840-6). As peripheral vasodilatation has been implicated in the progression of liver cirrhosis, AM may directly participate in the pathogenesis of the disease (Fabrega et al., 1997, supra; Fernandez-Rodriguez et al., 1998, supra; Guevara et al., 1998, supra; Kojima et al., 1998, supra).

Monoclonal antibodies directed to AM have been shown to inhibit tumor cell growth in a concentration-dependent manner, an effect that is reversed with the addition of exogenous AM (M. J. Miller et al., 1996, *J. Biol. Chem.* 271:23345-51). AM has also been found to be expressed in numerous and diverse cancer cell lines (M. J. Miller et al., 1996, supra), as well as in small and non-small cell lung carcinomas (A. Martínez et al., 1995, *Endocrinology* 136:4099-105). In addition, AM binds to specific sites on human malignant melanoma cells and exogenous AM stimulates melanoma cell growth (A. Martínez et al., 1997, *Endocrinology* 138:5597-604). Moreover, cyclic AMP levels in tumor cells increases in the presence of AM (M. J. Miller et al., 1996, supra; K. Takahashi et al., 1997, *Peptides* 18:1117-24), indicating that AM may act as a autocrine growth factor to promote neoplastic proliferation (M. J. Miller et al., 1996, supra).

It has been demonstrated that AM inhibits insulin secretion in a dose-dependent manner, while neutralizing monoclonal antibodies directed to AM increases insulin release by 5-fold; this effect was reversed by the addition of synthetic AM (A. Martínez, 1996, *Endocrinology* 137:2626-32). Additionally, intravenous injection of AM reduces the levels of insulin in the bloodstream with a concomitant increase in circulating glucose (Martínez, 1996, supra). These observations implicate AM as an insulin regulatory factor involved in diabetes and obesity.

In clinical experiments, septic patients showed extremely elevated plasma AM concentrations, and those with acute renal failure had markedly elevated plasma AM levels during the early course of the illness; however, AM levels declined rapidly during the recovery course (Y. Hirata et al., 1996, *J. Clin. Endocrinol. Metab.* 81:1449-53). Similarly, patients with systemic inflammatory response syndrome, pancreatitis, traumatic shock, or severe sepsis show significantly increased plasma levels of AM, and these levels increased in proportion to the severity of illness (S. Ueda et al., 1999, *Am. J. Respir. Crit. Care Med.* 160:132-6). AM levels also correlate with sepsis markers such as the Acute Physiology and Chronic Health Evaluation II score and the peak multiple organ failure score, indicating that AM levels can be used to evaluate the severity of sepsis and can serve as an early predictor of organ failure and outcome (Ueda et al., 1999, supra).

The diverse actions of AM are thought to be orchestrated by temporal and/or tissue-specific regulatory factors. The activities of several other peptide hormones are modulated by binding proteins present in extracellular fluids. For example, one of the most well characterized classes/families of hormone binding proteins are the insulin-like growth factor binding proteins (IGF-BPs). IGF-BPs can direct, enhance, or block the action of IGF-1 on cells by regulating the ability of IGF-1 to bind to cell surface receptors (D. R. Clemmons et al., 1998, *Mol. Cell. Endocrinol.* 140: 19-24).

The detection, isolation and identification of AM-binding proteins, or families of such proteins, are therefore important goals for the further understanding of AM regulation and function in both normal and disease states in animals, including mammals, preferably humans. Such AM-binding proteins may stabilize or destabilize AM, direct AM to specific sites, modulate AM-binding to its receptor, or otherwise interact with AM to regulate or modulate its activity and/or function. AM-binding proteins may thereby provide a molecular basis for the actions of AM on different tissues, at different times, and in different illnesses and disease states.

Moreover, as a result of the present invention, AM-binding proteins can be used to quantify plasma AM levels in order to diagnose and/or monitor the presence or progression of diseases which are characterized by altered concentrations of circulating AM. AM-binding proteins can also be used to prevent or treat diseases caused or exacerbated by elevated levels of plasma AM by administrating AM-binding proteins in dosages sufficient to bind to AM and thereby block AM activities or interactions with other components.

SUMMARY OF THE INVENTION

The present invention provides newly developed methods for the detection, isolation and identification of AM-binding proteins, or functional portions thereof, for example, in the form of functional AM polypeptides or peptides. The present invention further provides diagnostics and treatments that utilize the AM-binding proteins, polypeptides, or peptides. The invention also provides a newly identified complex of AM and an AM-binding protein identified herein as human complement factor H (fH; factor H), (GenBank Accession No. CAA30403). Human complement factor H has been determined to be a marker for urinary bladder carcinomas (R. Heicappell et al., 1999, Eur. Urol. 35:81-7). In accordance with the present invention, novel therapeutics which utilize the AM binding protein factor H, or related AM-binding proteins or peptides, are provided for treating cancers, particularly, urinary bladder cancer.

It is an object of the present invention to provide methods of isolating AM-binding proteins, wherein AM is conjugated with a label or marker and incubated with cellular or extracellular lysates. The label or marker may be radioactive or non-radioactive, and is preferably non-radioactive. In accordance with the aspect of the invention related to non-radioactive labels or markers of AM, AM is labeled with fluorescent, chemiluminescent, or immunoreactive molecules, or epitope tags.

It is another object of the present invention to provide diagnostic reagents comprising AM-binding proteins or peptides to detect and/or monitor levels of AM in body fluid samples, including cell and tissue lysates and extracts.

It is yet another object of the present invention to provide methods of using AM-binding proteins or peptides as diagnostic reagents for quantifying AM levels, particularly circulating AM levels. Such methods are useful for disease diagnosis, for determining disease severity, and for following the course of treatment for diseases characterized by altered or abnormal AM levels. These diseases include heart and pulmonary diseases, liver cirrhosis, cancers, diabetes, sepsis, inflammation, and other disorders characterized by altered AM plasma concentrations.

It is still another object of the present invention to provide improved quantitative assays for detecting AM in serum, utilizing a chaotropic agent, e.g., sodium thiocyanate to dissociate AM from factor H prior to serum extraction and quantitation of AM.

It is a further object of the present invention to provide quantitative assays for detecting AM, or peptides thereof, using factor H, or related AM-binding polypeptides or peptides, instead of anti-AM antibodies to capture the AM ligand.

It is also a further object of the present invention to provide kits for detecting AM comprising AM-binding proteins, e.g., factor H, or AM-bindable peptides thereof.

It is yet a further object of the invention to provide pharmaceutical compositions comprising AM-binding proteins or peptides. In accordance with the present invention, such pharmaceutical compositions are used to treat conditions caused or exacerbated by abnormal, e.g., elevated, levels of plasma AM. These conditions include liver cirrhosis, cancers, diabetes, or other disorders caused or exacerbated by elevated AM plasma concentrations.

It is another object of the present invention to provide a novel complex of AM and the AM-binding protein factor H. The complex is referred to herein as AM/fH.

It is also an object of the present invention to provide isolated and substantially purified antibodies that have specific binding affinity or immunoreactivity with an AM/AMBP complex or fragments of the complex, preferably the AM/fH complex or fragments derived therefrom.

It is another object of the present invention to use the above said antibodies in methods to detect the AM/AMBP complex or the AM/fH complex in vivo or in vitro or treat AM-related conditions, such as cancer or diabetes.

It is still another object of the present invention to provide kits for measuring concentrations of AM/AM-binding protein complex comprising anti-AM/AMBP antibodies, particularly anti-AM/fH antibodies.

It is an additional object of the present invention to provide antagonist agents that inhibit AM, factor H, or AM/fH activity.

It is yet another object of the present invention to provide methods of treating cancer by administering one or more antagonist agents in amounts sufficient to inhibit AM, factor H, or AM/fH activity.

It is also an object of the present invention to provide methods of treating cancer by administering antibodies that specifically bind to the AM/factor H in amounts sufficient to bind to the AM/factor H complex and inhibit AM/fH activity.

Further objects and advantages of the present invention will be apparent from the detailed description set forth below.

DESCRIPTION OF THE FIGURES

The appended figures are presented to further describe the invention and to assist in its understanding through clarification of its various aspects.

FIG. 4 illustrates the isolation of AMBP-1.

FIG. 5 illustrates the biochemical characterization of AMBP-1 as human complement factor H. FIG. 5A shows Coomassie Blue and glycoprotein staining (GelCode Glycoprotein Staining Kit, Pierce, Rockford, Ill.) of samples separated by SDS-PAGE. Lane 1: horseradish peroxidase (5 μg), a glycosylated protein used as positive control; Lane 2: soybean trypsin inhibitor (5 μg), a non-glycosylated protein used as negative control; Lane 3: AMBP-1 (2 μg). FIG. 5B shows Coomassie Blue staining of samples separated by electrophoresis on a isoelectric focusing gel pH 3-10 (Novex, San Diego, Calif.). Lane 1: isoelectric focusing markers; Lane 2: AMBP-1 (4 μg). FIG. 5C shows Western blot analysis of samples with an anti-factor H antibody. Lane 1: AMBP-1 (100 ng); Lane 2: AMBP-1 (200 ng); Lane 3: commercially available human factor H (50 ng); Lane 4: human plasma (0.2 μl). FIG. 5D shows non-radioactive ligand blotting of 1 μg AMBP-1 (Lane 1) and factor H (Lane 2). FIG. 5E shows ligand blotting of AMBP-1 (250 ng) under unreduced (Lane 1) or reduced conditions (Lane 2). FIG. 5F shows binding of fluorescein-labeled AM (50 nM) to a multi-well plate coated with factor H (5 ng/well) is competitively inhibited by increasing concentrations of unlabeled AM (•). In contrast, AM binding to factor H is not affected by PAMP (*) or CGRP(○). Results represent one of two independent experiments. Values represent mean and standard deviation of three determinations. "$B/B_0$" indicates the ratio of signals generated in the presence/absence of unlabeled competitor.

FIG. 6 illustrates the dissociation of the AM/fH complex. FIG. 6A: Purified AMBP-1 (fraction #48) was separated by electrophoresis and transferred to a membrane. After incubation with fluorescein-labeled AM and prior to the final development, the membrane was incubated under various conditions (neutral pH unless indicated). Lane 1: PBS; Lane 2: pH 11.5; Lane 3: pH 2.5; Lane 4: 4M NaCl; Lane 5: 4M NaCl pH 11.5; Lane 6: 4M NaCl pH 2.5; Lane 7: 1% SDS; Lane 8: 3M Urea; Lane 9: 3M Guanidine-HCl; Lane 10: 3M sodium thiocyanate (NaSCN); Lane 11: 50% ethylene glycol pH 11.5; Lane 12: 50% ethylene glycol; Lane 13: 1% β-mercaptoethanol. The band represents the AM/fH complex that remains unaffected by the incubation conditions. FIG. 6B shows dissociation of the AM/fH complex in a multi-well plate assay system. Factor H coated wells were incubated with fluorescein-labeled AM, and prior to the development of the assay, wells were incubated in PBS with 3M NaSCN pH 7.4 for various time periods. Values represent the mean and standard deviation of six determinations. $B/B_0$ represents the percentage of total binding.

FIG. 7 illustrates Western blot analysis of factor H and AM after C18 extraction. FIG. 7A shows human plasma (1 ml) processed with a SEP PAK® C18 solid-phase extraction cartridge and analyzed by Western blotting with anti-factor H antibodies. Lane 1: commercially available human factor H (10 ng); Lane 2: whole human serum (0.5 μl); Lane 3: unbound fraction (1 μl). Lane 4, bound fraction (1 μl). FIG. 7B shows human plasma (1 ml) processed with a SEP-PAK® C18 solid-phase extraction cartridge and analyzed by Western blotting following immunoprecipitation with anti-AM antibodies. Lane 1: synthetic AM (1 ng); Lane 2: fraction immunoprecipitated with normal rabbit serum (30 μl); Lane 3: fraction immunoprecipitated with rabbit anti-AM antibody (30 μl).

FIG. 9 illustrates the effect of factor H on AM activity.

FIG. 10 illustrates the effect of AM on factor H activity. C3b (104 kDa α' chain and 71 kDa β chain) was incubated 24 hr at 37° C. with factor H, factor I, and various peptides. Cleavage of the C3b α' chain produced three bands with molecular weights 68 kD, 43 kD, and 42 kD. FIG. 10A shows the effect of various AM concentrations on the cofactor activity of factor H. FIG. 10B shows the effect of AM on factor H activity compared to the effect of the structurally related peptide CGRP and the gene-related peptide PAMP on factor H. Each figure shows a representative example of three different experiments.

FIG. 11 illustrates Northern blot analysis of factor H (4.3 kb) and factor H-like (FHL-1, 1.8 kb) message expression in human tumor cell lines. FIG. 11A shows the results of Northern blot analysis using the factor H probe. FIG. 11B shows ethidium bromide staining to show the amount of total RNA loaded in each well. "CA" indicates carcinoma; "BAC" indicates bronchiolaolveolar carcinoma; "vSCLC" indicates variant small cell lung cancer; "Adeno CA" indicates adenocarcinoma; "Squamous CA" indicates squamous cell carcinoma.

FIG. 12 illustrates immunohistochemical labeling of factor H in rat pancreas. Anti-factor H antibodies localized factor H to cells in the islets of Langerhans (FIG. 12A). This localization showed a granular pattern at higher magnification (FIG. 12B). Anti-factor H antibodies also localized factor H to some exocrine acini (FIG. 12C). Affinity purified anti-factor H antibodies showed the same pattern of staining (FIG. 12D). Arrows indicate regions of factor H localization.

FIG. 13 illustrates immunofluorescence labeling of insulin (FIGS. 13A, 13E, and 13I), factor H (FIGS. 13B, 13F, and 13J), and either glucagon (FIG. 13C), somatostatin (FIG. 13G), or pancreatic peptide (FIG. 13K) in rat pancreas. The fourth column (FIGS. 13D, 13H, and 13L) represents an composite of the triple label. In all cases factor H (FH) colocalizes with insulin (INS) in the central β cells, and factor H is absent from the peripheral cells which produce somatostatin (SST), glucagon (GLUC), or pancreatic polypeptide (PP). Samples were analyzed by confocal microscopy.

DETAILED DESCRIPTION OF THE INVENTION

Figure 1:
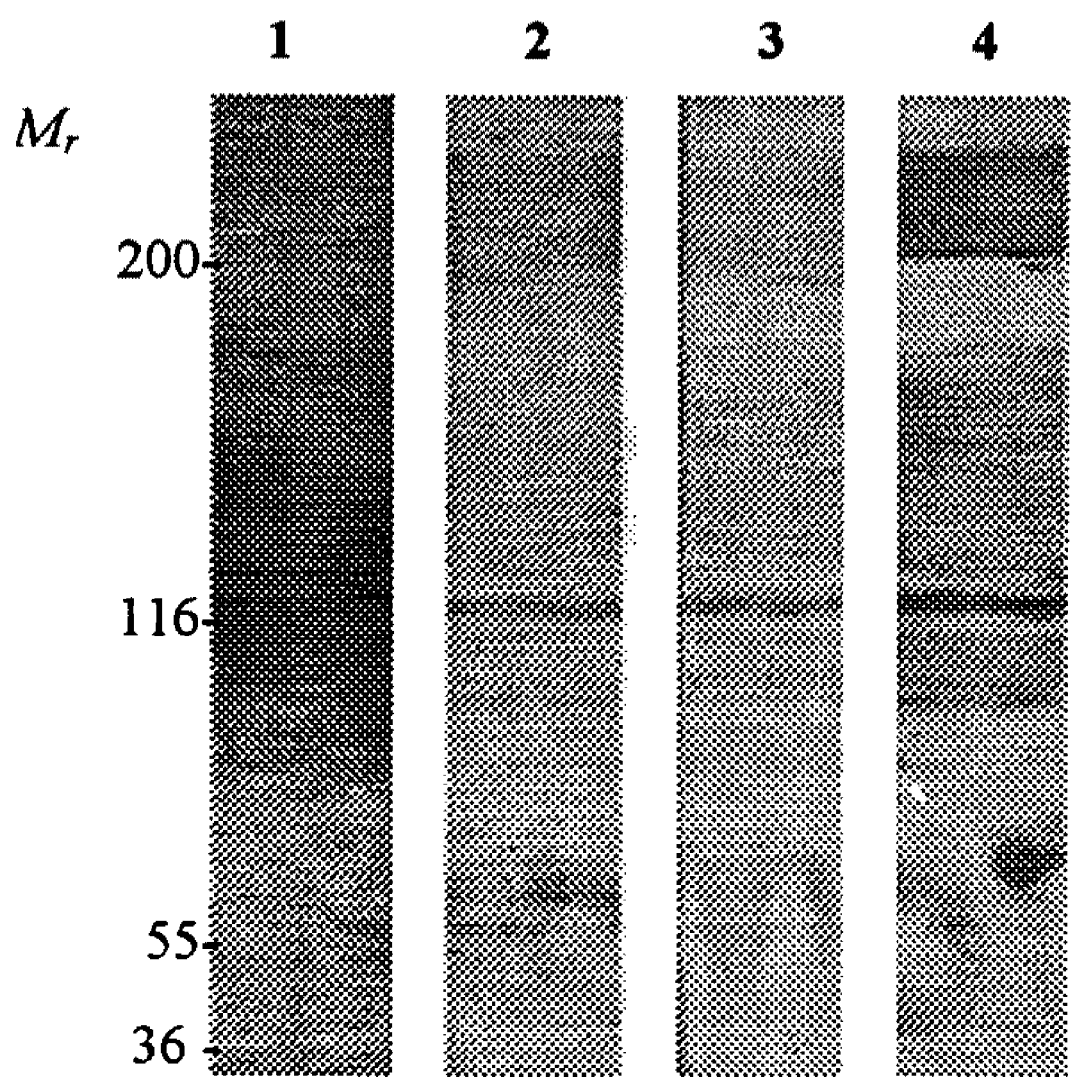
FIG. 1 illustrates the detection of plasma-derived AM-binding protein 1 (AMBP-1) binding to labeled AM. AMBP-1 has been identified herein as human complement factor H (factor H), based on comparative biochemical and protein determinations and sequence information provided in publicly available databases. Lane 1: AM radiolabeled with $^{125}$iodine; Lane 2: AM labeled with biotin; Lane 3: AM labeled with fluorescein; Lane 4: AM labeled with dinitrophenol. The band in each lane represents the complex formed by labeled AM binding to AMBP-1 (factor H).

One embodiment of the present invention encompasses a ligand blotting assay in which AM as ligand is labeled with a radioactive or non-radioactive molecule, marker, or tag, and used as a probe to identify an AM-binding protein or an AM-binding fragment thereof. Preferred in the present invention are non-radioactively labeled AM ligands.

Labeling of AM

Numerous methods may be used for the non-radioactive labeling of AM or related peptides. For example, coupling agents such as aldehydes, carbodiimides, dimaleimides, iminodiacetates, succinimides, aminobenzamidines and related compounds can be used to conjugate AM peptides with fluorescent, chemiluminescent, or chemical labels. Examples of nonradioactive labels that can be used include, but are not limited to, fluorescent labels such as fluorescein and its derivatives, e.g., fluorescein isothiocyanate, rhodamine and its derivatives, dansyl, and umbelliferone; chemiluminescers such as 2,3-dihydrophthalazine-dione, and chemical groups such as dinitrophenol (DNP), digoxigenin, and biotin.

AM or peptides derived therefrom can also be tagged with amino acid sequences that carry immunoreactive epitopes. A non-limiting list of suitable epitope tags includes c-myc, haemagglutinin (HA), polyhistidine (6x-HIS), GLU-GLU, and DYKDDDDK (FLAG®) tags. Epitope tags can be added to polypeptides or peptides by a number of established methods. The DNA sequences of epitope tags can be inserted into polypeptide or peptide coding sequences as oligonucleotides or via primers used in PCR amplification. Alternately, polypeptide or peptide coding sequences can be cloned into specific vectors that create fusions with epitope tags; for example, pRSET vectors (Invitrogen Corp., San Diego, Calif.).

The complete AM peptide, or fragments derived from AM, preferably having the same or equivalent function as AM, can be used. AM peptides that may be useful have been described in patent application U.S. Ser. No. 09/011,922, filed Feb. 17, 1998 to F. Cuttitta et al.

In another aspect of the present invention, AM can be tagged or marked with radioactive isotopes, such as $^{125}$I, $^{135}$I, $^{35}$S, $^{14}$C, or [$^3$H]-thymidine, as nonlimiting examples. Those having skill in the art know how to label proteins and peptides with radioactive isotopic labels using methods and protocols routinely practiced in the art. For example, AM can be labeled by incorporating $^{14}$C or $^{35}$S labeled amino acids during protein synthesis in host cells or cell-free expression systems (see below). This radiolabeled AM can then be isolated and assayed for its binding to the AM-receptor to confirm its biological function.

Identification of AM-Binding Proteins

Candidate AM-binding proteins, polypeptides, or peptides derived therefrom, can be identified and analyzed by many well-known methods in the art (see T. E. Creighton, Ed., 1997, *Proteins Structure: A Practical Approach*, IRL Press at Oxford Press, Oxford, England). As used herein, the terms protein and polypeptide are synonymous. Peptides are defined as fragments or portions of proteins or polypeptides, preferably fragments or portions having the same or equivalent function or activity as the complete protein.

AM-binding proteins can be obtained from biological samples, such as plasma and body fluid samples of animals, including cells and tissues and lysates or extracts derived therefrom. Suitable animal sources of AM-binding proteins include birds, fish, insects, and mammals, including humans. The proteins obtained from these sources can be separated into bands by size fractionation using sodium dodecylsulfate-polyacrylamide gel electrophoresis (SDS-PAGE) and transferred by electroblotting, for example, onto a suitable solid-phase matrix, support, or membrane (e.g., glass or polymer beads or nylon reinforced nitrocellulose or polyvinylidene fluoride). The support can then be incubated with labeled AM. Proteins/polypeptides that correspond to bands that exhibit specific binding with labeled AM are then identified, isolated/purified, and analyzed by amino acid analysis and Edman degradation to determine the amino acid sequence of peptides derived therefrom.

Sequences determined from Edman degradation can be compared with subject sequences in available databases such as, without limitation, GenBank, SwissProt, BLOCKS, and Pima II. These databases, which contain previously identified and annotated sequences, may be searched for the full-length polypeptide and gene sequence using, for example, Basic Local Alignment Search Tool (BLAST; S.F. Altschul, 1993, *J. Mol. Evol.* 36:290-300; S. F. Altschul et al., 1990, *J. Mol. Biol.* 215:403-10).

In cases where the full-length sequences of AM-binding proteins are not available, extended or overlapping partial clones may be obtained by techniques conventionally known and practiced in the art. Non-limiting examples of such techniques include hybridization to plasmid or phage libraries of genomic DNA or cDNA; PCR from the same libraries using AM-binding protein primer pairs; or hybridization or PCR directly to genomic DNA or cDNA. These clones may then be sequenced and assembled into full-length genes using the fragment sequence alignment program (PHRAP; Nickerson et al., 1997, *Nucleic Acids Res.* 25:2745-2751).

Purification of AM-Binding Proteins

Isolated AM-binding proteins or peptides may be used in diagnostics and treatments according to the present invention. An isolated protein or peptide as used herein refers to a component that is removed from its original environment (for example, its natural environment if it is naturally occurring). An isolated protein or peptide contains less than about 50%, preferably less than about 25%, and most preferably less than about 10%, of the components with which it was originally associated. Preferably, an isolated polypeptide or peptide is at least about 80-90% pure, more preferably at least about 90-100% pure.

Both naturally occurring and recombinant forms of the AM-binding proteins or peptides can be used. Methods for directly isolating and purifying polypeptides from natural sources such as cellular or extracellular lysates are well-known in the art (see E. L. V. Harris and S. Angal, Eds., 1989, *Protein Purification Methods: A Practical Approach*, IRL Press, Oxford, England). Such methods include, without limitation, preparative disc-gel electrophoresis, isoelectric focusing, high-performance liquid chromatography (HPLC), reversed-phase HPLC, gel filtration, ion exchange and partition chromatography, and countercurrent distribution, and combinations thereof. Naturally occurring polypeptides can be purified from many possible sources, for example, plasma, body cells and tissues, or body fluids.

To produce recombinant AM-binding proteins or peptides, DNA sequences encoding the AM-binding proteins or peptides are cloned into a suitable vector for expression in intact host cells or in cell-free translation systems (see J. Sambrook et al., 1989, *Molecular Cloning: A Laboratory Manual*, 2$^{nd}$ Edition, Cold Spring Harbor Press, Cold Spring Harbor, N.Y.). Prokaryotic and eukaryotic vectors and host cells may be employed. The particular choice of vector/host/translation system is not critical to the practice of the invention. DNA sequences can be optimized, if desired, for more efficient expression in a given host organism. For example, codons can be altered to conform to the preferred codon usage in a given host cell or cell-free translation system using techniques routinely practiced in the art.

Cloning vectors include, but are not limited to pUC, pBluescript (Stratagene, La Jolla, Calif.), pET (Novagen, Inc., Madison, Wis.) and pREP (Invitrogen Corp.) plasmids. Vectors can contain one or more replication and inheritance systems for cloning or expression, one or more markers for selection in the host, e.g. antibiotic resistance, and one or more expression cassettes. The inserted coding sequences can be synthesized by standard methods, isolated from natural sources, or prepared as hybrids. Ligation of the coding sequences to transcriptional regulatory elements (e.g., promoters, enhancers, and/or insulators) and/or to other amino acid encoding sequences can be carried out using established methods.

For some purposes, it may be preferable to produce peptides or polypeptides in a recombinant system wherein the peptides or polypeptides carry additional sequence tags to facilitate purification. Such markers include epitope tags (described above) and protein tags, for example, glutathione-S-transferase (GST), green fluorescent protein (GFP), and maltose binding protein (MBP). Protein tags are attached to peptides or polypeptides by several well-known methods. As a non-limiting example, the coding sequence of a polypeptide or peptide can be cloned into a vector that creates a fusion between the polypeptide or peptide and a protein tag of interest. Suitable vectors include, without limitation, the exemplary plasmids, pGEX (Amersham Pharmacia Biotech, Inc., Piscataway, N.J.), pEGFP (CLONETECH Laboratories, Inc., Palo Alto, Calif.), and pMAL™ (New England BioLabs, Inc., Beverly, Mass.). The tagged polypeptide or peptide can then be purified from a crude lysate of the translation system or host cell by chromatography on an appropriate solid-phase matrix.

Suitable cell-free expression systems for use in accordance with the present invention include rabbit reticulocyte lysate, wheat germ extract, canine pancreatic microsomal membranes, *E. coli* S30 extract, and coupled transcription/translation systems (Promega Corp., Madison, Wis.). These systems allow the expression of recombinant polypeptides or peptides upon the addition of cloning vectors, DNA fragments, or RNA sequences containing coding regions and appropriate promoter elements.

Host cells for recombinant cloning vectors include bacterial, archebacterial, fungal, plant, insect and animal cells, especially mammalian cells. Of particular interest are *E. coli, Bacillus subtilis, Staphylococcus aureus, Saccharomyces cerevisiae, Schizosaccharomyces pombe, Neurospora crassa*, SF9, C129, 293, NIH 3T3, CHO, COS, and HeLa cells. Such cells can be transformed, transfected, or transduced, as appropriate, by any suitable method including electroporation, $CaCl_2$—, LiCl—, LiAc/PEG-, spheroplasting-, Ca-Phosphate, DEAE-dextran, liposome-mediated DNA uptake, injection, microinjection, microprojectile bombardment, or other established methods.

Antibody-based methods may also be used to purify natural or recombinantly produced AM-binding proteins or peptides. Antibodies that recognize these polypeptides, or peptides derived therefrom, can be produced and isolated using methods known and practiced in the art. AM-binding polypeptides or peptides can then be purified from a crude lysate by chromatography on antibody-conjugated solid-phase matrices (see E. Harlow and D. Lane, 1999, *Using Antibodies: A Laboratory Manual*, Cold Spring Harbor Laboratory, Cold Spring Harbor, N.Y.). Other purification methods known and used in the art may also be employed.

The AM-binding protein Human Complement Factor H (fH)

In a preferred embodiment of the present invention, the AM-binding protein is human complement factor H. Factor H was originally identified as an important modulator of the complement cascade of the immune system (see M. P. Dierich, 1988, *Mol. Immunol.* 25:1043-51). Specifically, factor H forms a complex with factor 1, and the fH-fI complex selectively degrades C3b, inactivates the C3 convertase, and competes for factor B binding to C3b (P. F. Zipfel, et al., 1999, *Immunopharmacol.* 42:53-60). In addition, factor H can bind to the integrin receptor (CD11b/CD18) expressed in a variety of human tissues, and bind to certain surface glycosaminoglycans present on both prokaryotic and eukaryotic cells (P. F. Zipfel, et al., 1999, *Immunopharmacol.* 42:53-60).

The full length cDNA (4.3 kb) for human factor H has been cloned and sequenced and found to undergo alternative gene splicing to give rise to a shorter message (1.8 kb)(P. F. Zipfel et al., 1999, *Mol. Immunol.* 36:241-8). This smaller message is translated into a truncated factor H molecule (43 kDa), denoted as factor H-like protein (FHL-1), that shares the complement regulatory functions of factor H(P. F. Zipfel et al., 1999, *Mol. Immunol.* 36:241-8). Structurally, factor H contains twenty short consensus repeats (SCRs), while FHL-1 contains seven SCRs. According to conventional nomenclature, factor H is represented as SCR 1-20 with FHL-1 being SCR 1-7 (P. F. Zipfel, et al., 1999, *Immunopharmacol.* 42:53-60). Notably, both factor H and factor H-like proteins have been used as markers for urinary bladder carcinomas (R. Heicappell et al., 1999, *Eur. Urol.* 35:81-7).

Figure 4A:
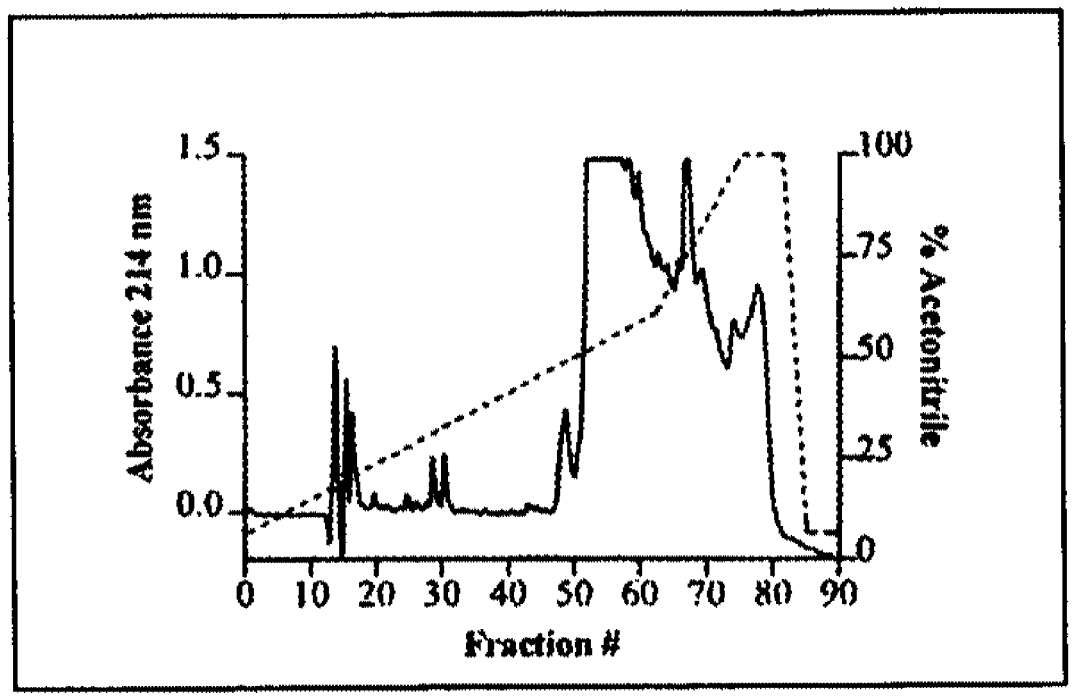
FIG. 4A shows fractionation of human plasma by reverse phase HPLC. The dotted line indicates the acetonitrile gradient.
Figures 4B, 4C:
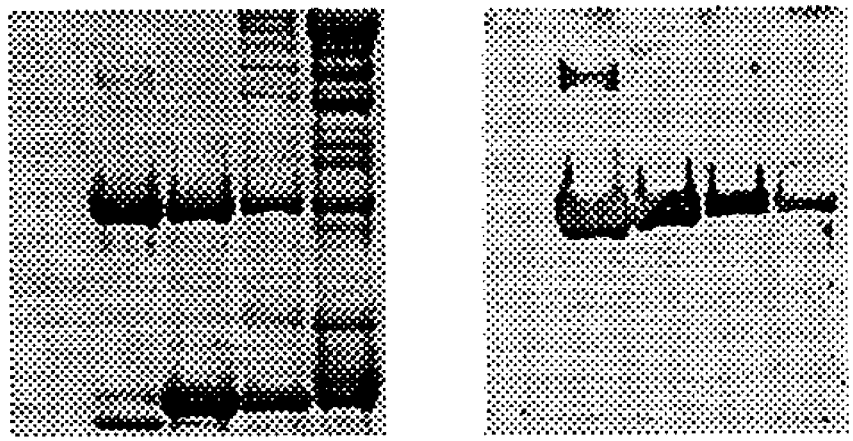
FIG. 4B shows Coomassie Blue staining of HPLC fractions 47-51.
FIG. 4C shows ligand blotting of HPLC fractions 47-51.

In accordance with the AM-binding protein isolation and identification methods described herein, the present inventors have demonstrated that factor H is an AM-binding protein isolated from human plasma. Specifically, a non-radioactive ligand blotting technique (Examples 1 and 2; FIG. 1) and HPLC/SDS-PAGE (Example 4; FIGS. 4A-4C) purification techniques allowed the isolation of the AMBP-1 protein. The purified protein was subjected to total amino acid analysis, N-terminal amino acid sequence, and mass spectrometry (Example 5; Table 1). In addition, purified AMBP-1 was compared with factor H, based on apparent molecular weight, glycosylation, AM-binding, and recognition by anti-factor H antibodies (Example 6; FIGS. 5A, 5C, and 5D). The results identified AMBP-1 as human complement factor H.

Additional experiments as described hereinbelow were conducted to characterize the AM/fH interaction (Example 7). These experiments showed that the AM/fH complex was not dissociated in acidic or high salt conditions (FIG. 6A). In contrast, the AM/fH complex was dissociated in the presence of chaotropic agents, such as NaSCN (FIG. 6A). The dissociation of the AM/fH complex by NaSCN was confirmed using a multi-well AM-binding assay, 96-well plate (Example 7). The displacement curve suggested the presence of two dissociation mechanisms, as shown by an initial rapid dissociation phase, followed by a slower dissociation phase (FIG. 6B).

Figure 8:
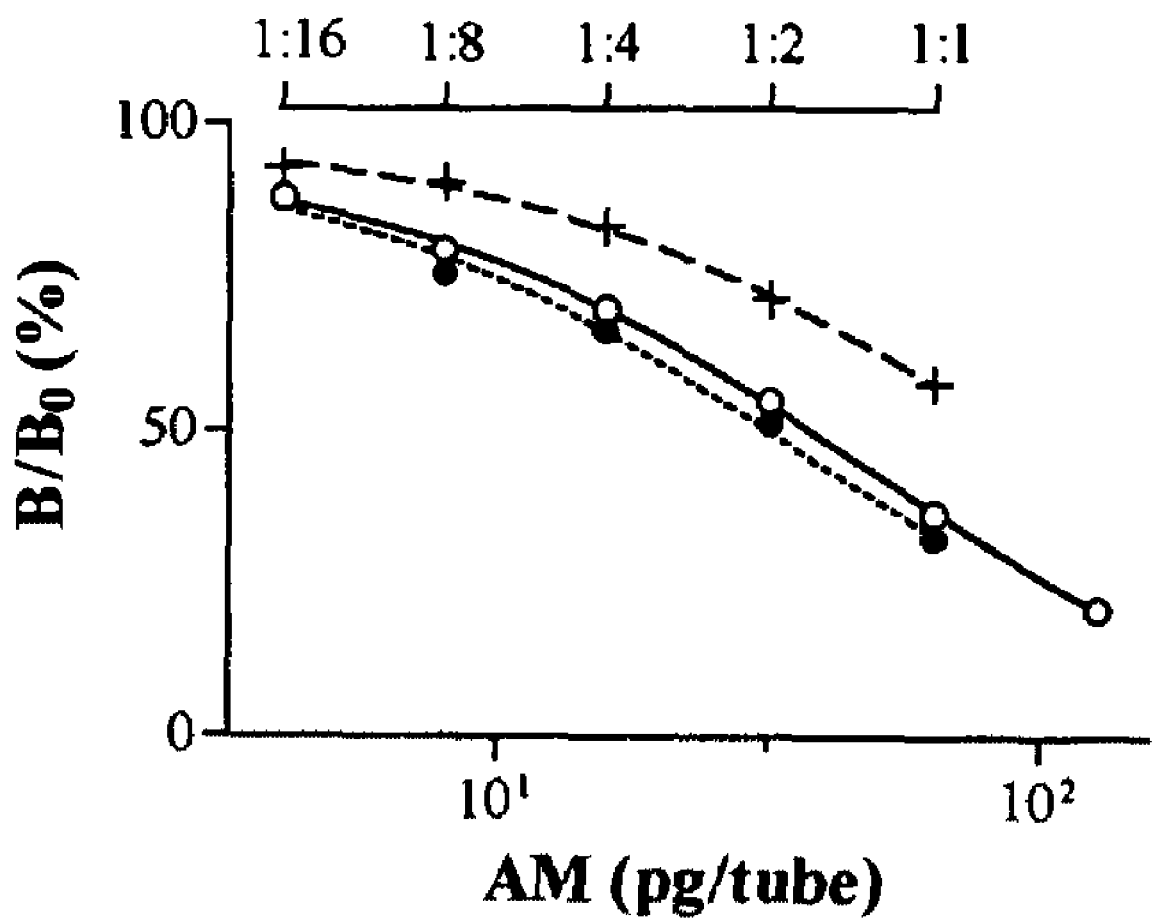
FIG. 8 illustrates competitive binding curves generated by human plasma in the AM radioimmunoassay. The dilution curves of plasma (4 ml) extracted following the standard protocol (+) or the NaSCN modification (•) were compared with the standard curve of synthetic AM (○). $B/B_0$ represents the ratio of radioactivity bound to that bound in the absence of added standard. The scale bar over the curves represents the different plasma dilutions.

Notably, the experiments described herein have shown that the AM/fH interaction interferes with the established methodology for quantification of circulating AM (Example 8). Thus, the routine radioimmunoassay (RIA) quantification of AM fails to account for the amount of AM bound to its binding protein, factor H. The inventors' studies have indicated that the standard C18 reverse-phase separation technique used to prepare plasma for RIA analysis effectively eliminates AMBP-1 (factor H) from the extract (T. H. Elsasser et al., 1999, *Endocrinology* 140:4908-4911; FIG. 7A). Further studies have demonstrated that AM is detected in both the unbound and the bound fractions following C18 reverse-phase separation (FIG. 7B), confirming that the traditional procedure does not recover the total amount of AM present in plasma. In addition, the inventors have performed a modified RIA analysis utilizing plasma pre-treated with a chaotropic agent, NaSCN, to dissociate AM/fH complexes in the plasma prior to extraction. The modified protocol detected AM levels that were twofold higher than those obtained with the standard technique (FIG. 8).

Figure 9A:
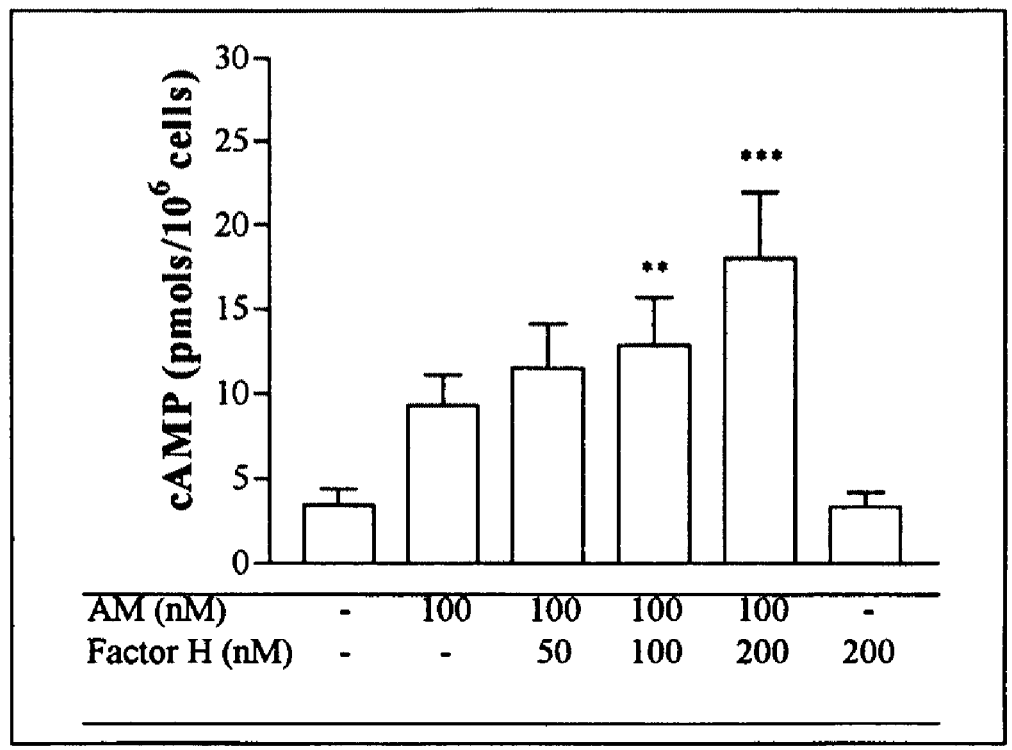
FIG. 9A shows the effect of factor H in AM mediated cAMP induction. Cyclic AMP was measured after incubating Rat-2 cells with AM and increasing concentrations of factor H. Incubations with AM and 100 or 200 nM factor H produced a significant increase in cAMP as compared to the levels obtained with AM alone ($p<0.01$ and $p<0.001$*, respectively). Incubation with factor H alone did not affect cAMP levels. Values represent mean and standard deviation of four independent determinations.
Figure 9B:
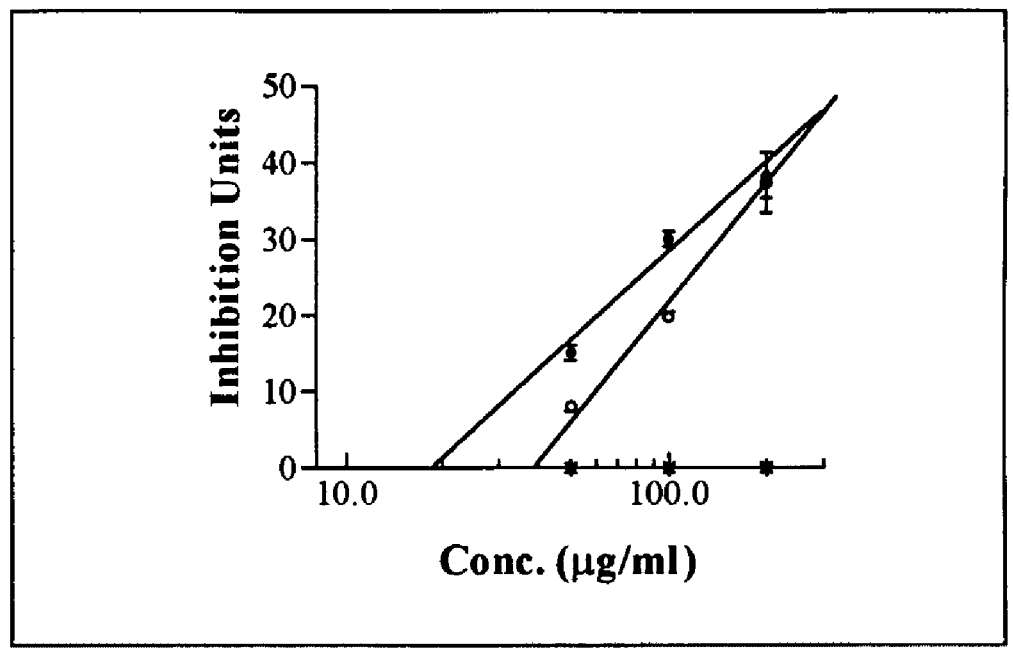
FIG. 9B shows the antimicrobial effect of AM (•), factor H (*), or AM in the presence of 50 μg/ml of factor H(○). Results are expressed in inhibition units (10 units correspond to 1 mm of diameter in the inhibition halo). MIC values were estimated by performing a linear regression and determining the x-intercepts. The MIC value for AM was 18.4±1.3 μg/ml, and increased to 35.4±1.1 μg/ml upon the addition of factor H ($p<0.001$). Values represent mean and standard deviation of the mean of eight determinations.

The inventors' experiments have further shown that factor H modulates AM activity, and AM modulates factor H activity. In particular, factor H enhances AM-mediated induction of cAMP in fibroblasts (Example 9; FIG. 9A), but suppresses the bactericidal activity of AM against *E. coli* (Example 9; FIG. 9B). Additionally, AM enhances fH/fI-mediated cleavage of C3b (Example 9; FIGS. 10A and 10B). Thus, the interaction of AM and factor H produces wide-ranging effects on both AM and factor H function.

In addition, experiments described in detail herein have shown that factor H and FHL-1 are highly expressed in non-small cell lung cancer cells, adenocarcinoma cells, and squamous cell carcinoma (Example 10; FIG. 11). Factor H and FHL-1 are also expressed in other solid tumor cells, such as breast, colon, ovary, and prostate carcinoma cells (FIG. 11). These results are consistent with recent findings, which have determined that factor H is expressed in a variety of human cancer cells (i.e., bladder cancer, breast cancer, and glioblastoma cells), and factor H facilitates cancer cells' resistance to complement-mediated cell lysis (N. S. Fedarko et al., 2000, *J. Biol. Chem.* 275:16666-16672; S. Junnikkala et al., 2000, *J. Immunol.* 164: 6075-6081; P. F. Zipfel et al., 1999, *Mol. Immunol.* 36:241-8).

Similarly, the inventors' studies have shown AM is expressed in several cancer cell lines, and monoclonal antibodies directed to AM inhibit tumor or cancer cell growth in a concentration-dependent manner (Martínez et al., 1995, supra; M. Garayoa et al., 2000, *Mol. Endocrinol.* 14(6):848-862; Martínez et al., 1997, supra; Miller et al., 1996, supra). Moreover, the experiments described herein show that AM potentiates fH/fI-mediated degradation of C3b (Example 9; FIGS. 10A and 10B). The sum of these observations indicates that the AM/fH complex may mediate cancer cells' resistance to complement-mediated cell lysis. Accordingly, antagonists that inhibit AM activity, inhibit factor H activity, or prevent the interaction of AM and factor H may act to decrease cancer cells' resistance to cell lysis. Such antagonist agents may thereby be used as cancer therapeutics.

Figure 14A:
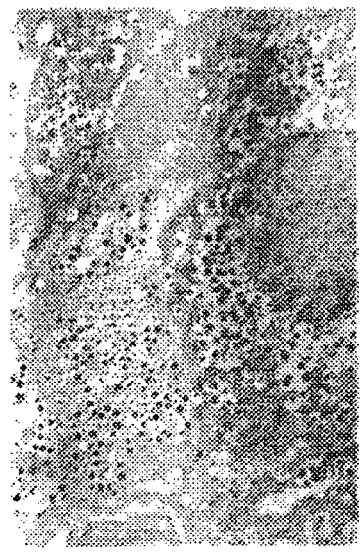
FIG. 14 illustrates immunogold labeling of factor H (small gold particles, 10 nm in diameter) and insulin (large particles, 20 nm) in rat pancreas. Low magnification images (FIG. 14A) show that factor H is localized to the characteristic secretory granules of the β cells, and factor H is absent from the surrounding endocrine cell types. High magnification images (FIG. 14B) show that factor H is predominantly localized to the lucent haloes, and insulin is predominantly localized to the dense granule cores. In addition, factor H is present in the secretory granules of some exocrine cells (FIG. 14C). Samples were analyzed by electron microscopy.
Figure 14B:
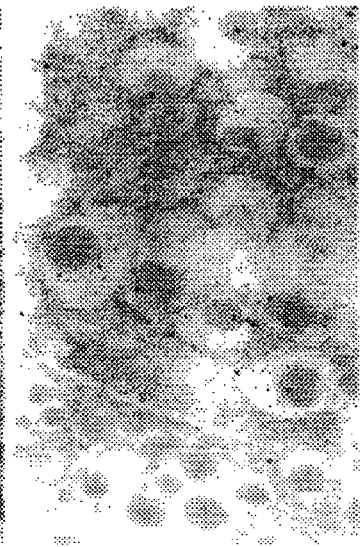
Figure 15A:
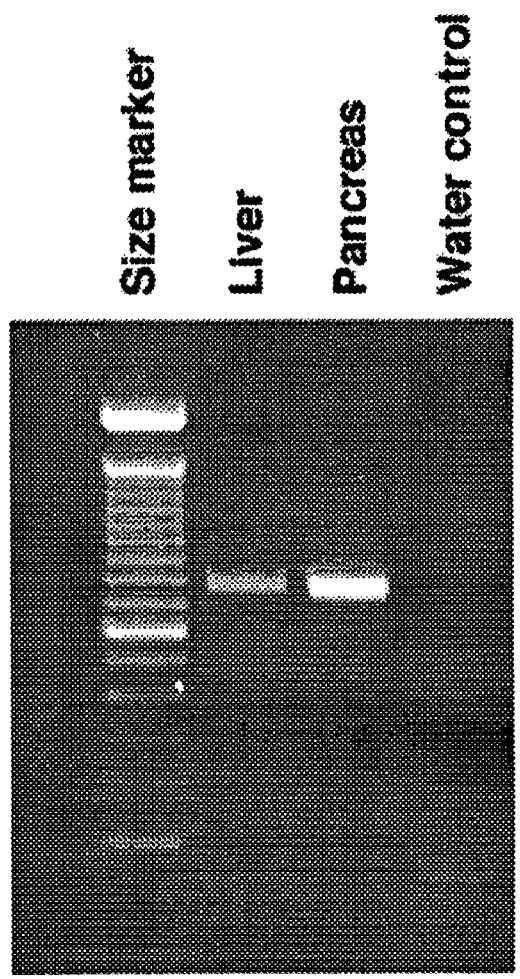
FIG. 15A shows the factor H PCR product (839 bp) amplified from mouse liver and pancreas cells. The PCR product was sequenced to determine that it contained mouse factor H sequence. RT-PCR results were confirmed by Southern blot analysis (FIG. 15B).

In a separate set of experiments described hereinbelow, the inventors have used immunohistochemical labeling (Example 11; FIGS. 12A-12D) and multiple immunofluorescence labeling followed by confocal microscopy (Example 12; FIGS. 13B, 13F, and 13J) to demonstrate that factor H is expressed by the β cells of rat pancreatic islets. Double immunogold staining under the electron microscope also showed colocalization of insulin and factor H within the same secretory granules (Example 13; FIG. 14B). Factor H was localized to electron-lucent haloes, whereas insulin was localized predominantly to electron-dense cores (FIG. 14B). The presence of factor H mRNA in the pancreas was confirmed by RT-PCR analysis (Example 14; FIG. 15A).

Figure 16A:
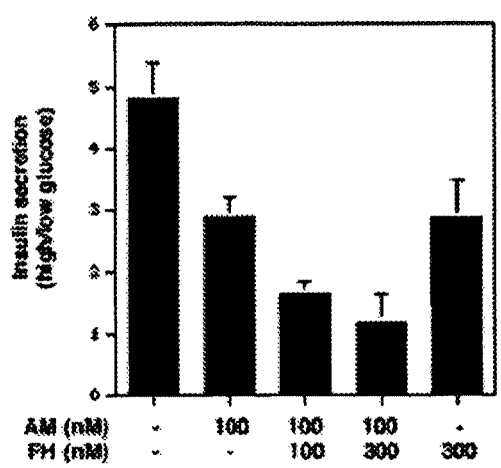
FIG. 16 illustrates the effect of factor H on insulin secretion. Incubated of islets with AM and/or factor H resulted in dose-dependent decreases in insulin secretion (FIG. 16A) and concomitant elevations on cAMP in the (FIG. 16B). A representative experiment is shown. Values for each treatment represent the mean and standard deviation of three independent wells. Insulin release is expressed as the ratio between the contents in the high glucose medium divided by the amount in the low glucose one to allow for variations in the number of secreting cells and/or their secretory efficiency. All values were statistically different (p<0.05) from the negative controls (first bar).
Figure 16B:
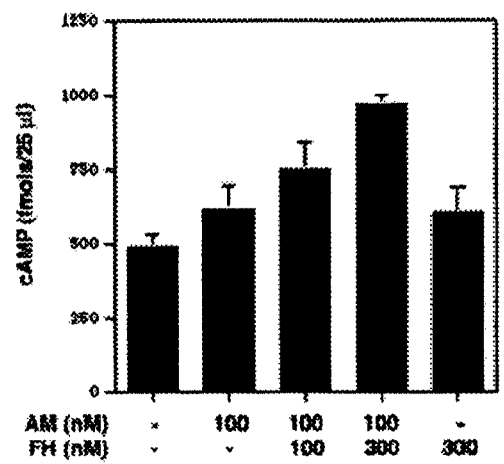

The inventors have previously determined that AM acts to reduce insulin secretion in the pancreas (A. Martínez, 1996, *Endocrinology* 137:2626-32). Thus, insulin secretion assays described herein have been used to investigate the role of factor H in pancreatic function (Example 15). Such assays have demonstrated that in the presence of AM, factor H induces a further reduction in insulin secretion with a concomitant elevation of cAMP (FIGS. 16A and 16B). Thus, antagonists that inhibit AM activity, inhibit factor H activity, or prevent the interaction of AM and factor H may act to increase insulin production. Such antagonist agents may thereby be used as therapeutics for conditions associated with reduced secretion of insulin (e.g., certain forms of type 2 diabetes and pheochromocytoma).

As indicated above, factor H can act to suppress complement-mediated cell lysis. In particular, factor H has been shown facilitate the resistance of bacterial cells (C. Neeleman et al., 1999, *Infect. Immun.* 67:4517-4524) and tumor cells (N. S. Fedarko et al., 2000, *J. Biol. Chem.* (in press)) to complement-mediated lysis. It is therefore possible that factor H normally protects β cells from complement-mediated lysis, and inhibition or reduced expression of factor H in β cells results in the autoimmune destruction of the cells. It is further possible that AM assists factor H in providing β cells with protection against complement-mediated lysis (see FIGS. 10A and 10B). In this way, factor H, the AM/fH complex, or functional fragments thereof may be used to treat conditions associated with autoimmune responses against p cells (e.g., type 1 diabetes).

Figure 17:
FIG. 17 illustrates the AM-binding proteins in various species detected by ligand blot analysis using $^{125}$I labeled human AM. The bands represent 120 kD or 140 kD moieties identified in the plasma or serum of the ten species analyzed.

The inventors have further demonstrated that plasma proteins from several species can specifically bind AM (T. H. Elsasser et al., 1999, *Endocrinology* 140:4908-4911; Example 16; FIG. 17). These AM-binding proteins have been identified by a radioligand blotting technique adapted from P. Hossenlopp et al. (1986, *Anal. Biochem.* 154:138-143). An AM-binding protein of molecular weight ($M_r$) 120 kD (under non-reducing conditions) has been observed in the plasma from most of the species analyzed, including humans. It is noted that the human 120 kD AM-binding protein corresponds to AMBP-1 (factor H), described in detail herein. Interestingly, an additional band of $M_r$ 140 kD has been observed in the plasma from ruminant species (i.e., calf, goat, and sheep). This band may represent a different protein or a different glycosylation pattern of the 120 kD protein. From these experiments, it is concluded that AM-binding proteins in animal and avian species may interact with AM to form AM/AMBP complexes similar to the AM/fH complex described herein.

Antibodies to AM-binding Proteins

The present invention provides antibodies that specifically recognize AM/AMBP complexes or fragments of these complexes, preferably AM/fH complexes or fragments derived therefrom. The present invention also provides assay methods comprising these antibodies to identify and/or distinguish among AM/AMBP complexes, preferably the AM/fH complex, in vivo or in vitro. For example, the methods involve the use of the antibodies, or labeled antibodies, that have been bound to a solid support or matrix in assays, e.g., immunoassays, to bind to the AM/AMBP complex, or a complex-specific fragment thereof.

In accordance with the invention, specific antibodies can be generated that recognize and bind to a specific complex of AM and an AM-binding protein to aid in the identification and detection or isolation of the complex. Preferred are antibodies that recognize and bind to the AM/fH complex, but do not recognize and bind to either AM or factor H alone. One method for utilizing the antibodies according to the present invention to isolate AM/AM binding protein complexes in a biological sample comprises providing a solid support to which are bound antibodies that recognize a specific AM/AM binding protein complex, or a complex-specific fragment thereof, contacting the support with the sample or an aliquot of the sample and eluting the complex that binds to the antibodies adsorbed onto the support. Another method for detecting AM/AM binding protein complexes in a sample comprises incubating the sample with antibodies that specifically recognize and bind to a complex of AM and an AM binding protein, or a complex specific fragment, under conditions that allow the antibodies to bind to the AM/AM binding protein complex and determining the binding of the antibodies to the complex.

As used herein, "antibody" refers to intact molecules as well as fragments thereof, such as Fab, F(ab)$_2$, and Fv, which are capable of binding an epitopic determinant. Antibodies that bind to the AM/AMBP complex, preferably AM/fH, can be prepared using the isolated AM/AMBP complex, preferably, AM/fH, or fragments containing small peptides specific to the complex as the immunogen or immunizing antigen. Antibodies can also be generated to AM-binding proteins or fragments derived therefrom using the isolated AM-binding protein or a derived fragment, as an immunogen. As will be appreciated by those having skill in the art, the immunogen can be conjugated to a carrier protein, if desired, to increase immunogenicity, particularly, if a small peptide is used. Commonly used carriers that are routinely used chemically coupled to peptides include serum albumins, i.e., bovine, sheep, goat, or fish serum albumin, thyroglobulin, and keyhole limpet hemocyanin. The coupled immunogen-carrier is then used to immunize a recipient animal (e.g., mouse, rat, sheep, goat, or rabbit).

The term "antigenic determinant" refers to that fragment of a molecule (i.e., an epitope) that makes contact with a particular antibody. When the AM/AMBP complex is used to immunize a host animal, numerous regions of the complex may induce the production of antibodies which bind specifically to a given region or three-dimensional structure on the complex; these regions or structures are referred to as antigenic determinants or epitopes. An antigenic determinant may compete with the intact antigen (i.e., the immunogen used to elicit the immune response) for binding to an antibody. Preferred are those antigenic determinants that are specific for the AM/AMBP complex.

AM/AMBP complex-specific antibodies according to the present invention include polyclonal and monoclonal antibodies. The antibodies can be elicited in an animal host by immunization with AM/AMBP complex-derived immunogenic components or can be formed by in vitro immunization (sensitization) of immune cells. The immunogenic components used as immunogens to elicit the production of antibodies can be isolated from plasma, recombinantly produced, or chemically synthesized. The antibodies can also be produced in recombinant systems programmed with appropriate antibody-encoding DNA. Alternatively, the antibodies can be constructed by biochemical reconstitution of purified heavy and light chains. The antibodies include hybrid antibodies, chimeric antibodies, humanized antibodies (see, for example, U.S. Pat. No. 5,585,089) and univalent antibodies. Also included are Fab fragments, Fab' and F(ab)$_2$ fragments of antibodies.

AM/AMBP complex as immunogens can be obtained using techniques as described above. For example, AM/AMBP complexes can be isolated and purified by excising the complexes from gels, particularly SDS-PAGE gels. Alternatively, recombinant AM and AM-binding proteins or related fragments can be co-expressed in a host cell or cell-free expression system and co-purified.

The immunogenic components of the AM/AM binding protein complex according to the invention are useful as antigens for preparing antibodies by standard methods. These antibodies, whether polyclonal or monoclonal, can be used, for example in an immobilized form bound to a solid support by well-known methods, to purify the immunogenic components, specifically, AM/AMBP complexes such as AM/fH, by immunoaffinity chromatography. In addition, the AM/AM binding protein complex can be used to screen antibodies, particularly monoclonal antibodies, that are generated as described below.

Hybridomas that produce monoclonal antibodies against the immunogenic components of the invention can be produced by well-known techniques. Hybridomas can be produced by the fusion of an immortalized cell line with a B-lymphocyte that produces the desired antibody. Alternatively, non-fusion techniques for generating immortal antibody-producing cell lines are possible, and are within the purview of the present invention (see Casali et al., 1986, *Science*, 234: 476). Immortalized cell lines are typically transformed mammalian cells, particularly myeloma cells of rodent, bovine, and human origin. Most frequently, rat or mouse myeloma cell lines are employed as a matter of convenience and availability.

Standard procedures can be used to select hybridomas, such as HAT (hypoxanthine-aminopterin-thymidine) selection. Hybridomas that secrete desired monoclonal antibodies can be selected by assaying the cells' culture medium by standard immunoassays, such as immunoblotting, ELISA (enzyme-linked immunosorbent assay; E. Engvall et al., 1971, *Immunochemistry*, 8:871-4; and D. J. Reen, 1994, *Methods Mol. Biol.* 32:461-6), RIA, or comparable assays. Antibodies can be recovered from the medium using standard protein purification techniques (see Tijssen, 1985, *Practice and Theory of Enzyme Immunoassays*, Elsevier, Amsterdam).

Agonists/Antagonists of AM, AM-binding Proteins, or Factor H

Agonists/antagonists that modulate AM activity, AM-binding protein (e.g., factor H) activity, or affect AM/AMBP (e.g., AM/fH) interaction may be employed as therapeutics. For example, antagonists that inhibit AM or factor H activity, or block AM/fH interaction may be formulated into pharmaceutical compositions that are used to inhibit the growth or proliferation of cancer cells, in particular, bladder cancer, breast cancer, and glioblastoma cells. Alternatively, agonists that increase AM activity and antagonists that decrease factor H activity or prevent AM/fH interaction can be formulated into pharmaceutical compositions and used to treat microbial infection, in particular, bacterial infection.

Modulators may comprise nucleic acids, oligonucleotides; polypeptides, peptides; oligosaccharides; lipids; antibodies, or derivatives or fragments of any of the foregoing, or other organic or inorganic molecules. Modulators can be identified using methods well-known in the art, such as, for example, by screening natural product libraries, fermentation libraries (encompassing plants and microorganisms), combinatorial libraries, compound files, and synthetic compound libraries for compounds that have the ability to bind to, and/or alter the function of AM or AM-binding protein (e.g., factor H). In particular, synthetic compound libraries can be obtained from commercial sources (e.g., Maybridge Chemical Co. (Trevillet, Cornwall, UK); Comgenex (Princeton, N.J.); Brandon Associates (Merrimack, N.H.); and Microsource (New Milford, Conn.). In addition, a rare chemical library can be obtained from Aldrich Chemical Company, Inc. (Milwaukee, Wis.). Alternatively, libraries of natural compounds in the form of bacterial, fungal, plant and animal extracts are available from, for example, Pan Laboratories (Bothell, Wash.), or are readily producible. Additionally, natural and synthetically produced libraries and compounds are readily modified through conventional chemical, physical, and biochemical means (Blondelle et al., 1996, *Trends in Biotech.* 14:60).

In one embodiment of the present invention, modulators may be identified by screening test molecules against AM or AM-binding protein (e.g.) nucleic acid or amino acid sequences in high-throughput assays. Such assays include without limitation genetic, biochemical, and ligand binding assays. Several methods of automated assays have been developed to permit screening of tens of thousands of compounds in a short period of time. These methods are particularly preferred. The use of high-throughput screening assays to test for modulators is greatly facilitated by the availability of large amounts of purified nucleic acid or amino acids sequences, as provided by the invention.

Ligand-binding assays can be used to detect binding of test compounds to particular sequences. The detection may involve direct measurement of binding. Alternatively, indirect indications of binding may involve stabilization of protein structure or disruption of a biological function. Non-limiting examples of useful ligand-binding assays are detailed below.

A useful method for the detection and isolation of binding proteins or peptides is the Biomolecular Interaction Assay (BIACORE®) molecular interaction analysis system (Pharmacia Biosensor, LKB Pharmacia, Sweden). The BIACORE® molecular interaction analysis system uses affinity purified anti-GST antibodies to immobilize GST-fusion proteins onto a sensor chip. A protein or peptide of interest is coated onto a chip and test compounds are passed over the chip. Binding is detected by a change in the surface plasmon resonance, which is an optical phenomenon that detects changes in refractive indices.

Alternatively, binding proteins can be identified by scintillation proximity assays (SPAS, described in U.S. Pat. No. 4,568,649). In a modified version of this assay, a tagged protein is attached to SPA beads, and test compounds are added. The tagged protein is then subjected to mild denaturing conditions (such as, e.g., heat, exposure to SDS, etc.) and a purified labeled chaperonin is added. If a test compound has bound to a tagged protein, the labeled chaperonin will not bind; conversely, if no test compound has bound, the chaperonin will bind.

In another approach, binding proteins or peptides can be identified using the binding assay described in Fodor et al., 1991, *Science* 251:767-773). Binding proteins can also be identified by in vitro mitochondrial-targeting assays (MTAs, based on Hurt et al., 1985, *EMBO J.* 4:2061-2068; Eilers and Schatz, *Nature*, 1986, 322:228-231). In accordance with MTAs, expression vectors are constructed to comprise a coding sequence for a polypeptide or peptide fused with a coding sequence for a mitochondrial localization signal. The resulting fusion proteins are produced and tested for importation into isolated mitochondria in the presence or absence of a test compound. It is predicted that a test compound that binds to a fusion protein will inhibit mitochondrial import.

In addition, binding proteins can be identified by the yeast two-hybrid system (Fields and Song, 1989, *Nature* 340:245-246; U.S. Pat. No. 5,283,173). The two-hybrid system assays the reconstitution of transcription activity through the association of a DNA-binding domain and a transcription activation domain of a transcriptional activator via protein-protein interactions. The yeast GAL4 transcriptional activator may be used in this system, although other transcription factors have been used. In brief, the GAL4 DNA-binding domain and the transcription activation domain are expressed, separately, as fusions to potential interacting polypeptides or peptides. If the two, coexpressed fusion proteins are targeted to the nucleus and interact, activation of a reporter gene (e.g. LacZ) produces a detectable phenotype. Related in vivo methods such as the three-hybrid (Licitra and Liu, 1996, *Proc. Natl. Acad. Sci. USA* 93:12817-12821), and reverse two-hybrid (Vidal et al., 1996, *Proc. Natl. Acad. Sci. USA* 93:10315-10320) systems may serve as alternative approaches.

As not all sequences are suitable for ligand binding assays, other types of assays, e.g., cell-free biochemical assays, are also contemplated for use. It will be appreciated by those skilled in the art that different types of assays can be used to detect different types of modulators.

Diagnostics Utilizing AM-Binding Proteins

Another embodiment of the present invention is directed to in vitro screening and diagnostic methods for detecting or monitoring the presence of AM or AM-binding proteins, preferably factor H or related proteins or peptides, in biological samples, e.g., serum, plasma, or cell and tissue extracts or lysate. For use as screening and diagnostic reagents in the methods, AM, AM-binding proteins or peptides, preferably factor H or related proteins or peptides, can be labeled by several established methods in the art. Polypeptides or peptides can be conjugated to labels using a number of different coupling agents as described above, and suitable labels include, without limitation, enzyme-based, fluorescent, chemiluminescent, radioactive, or dye molecules for use in assays that involve such labeled AM-binding proteins. Suitable assays that amplify the signals from the target or probe are well-known, e.g., biotin and avidin assays, and ELISAs can be used with the labeled AM-binding proteins to detect or monitor AM levels.

To provide a basis for the diagnosis of AM-related diseases associated with abnormal levels of AM, a normal or standard profile for AM expression may be established. This can be accomplished by incubating body fluids, tissue preparations, or cell lysates or extracts, for example, obtained from normal subjects, either animal or human, under conditions suitable for binding with labeled AM-binding proteins or peptides. Standard binding levels of AM to AM-binding proteins or peptides may be quantified by comparing the values obtained from normal subjects with those obtained from a standard or control sample in which a known amount of substantially purified AM is used. Standard values obtained from normal samples can be compared with values obtained from samples from subjects who are symptomatic for illness. A significant deviation between standard and test or experimental values is then used to determine the presence and severity of a disorder or disease involving abnormal or elevated levels of AM, particularly, circulating AM in plasma.

Following a diagnosis of a disorder or disease, and initiation of a treatment, binding assays can be repeated on a regular basis to evaluate whether the levels of AM, e.g., plasma AM, in the patient changes, or begins to approximate that which is observed in a normal individual. The results obtained from successive assays can be used to show the efficacy of treatment over a period of time, ranging from several days to months.

Additionally, AM-binding proteins or peptides may be included as reagents in AM detection or diagnostic kits. Suitable kits may include one or more of the following components:

i) one or more AM-binding proteins or peptides, preferably factor H or related functional peptides thereof; the included AM-binding proteins or peptides may be pre-labeled; alternatively, the AM-binding proteins or peptides may be unlabelled and the ingredients for labeling may be included in the kit in separate containers; and ii) reaction components such as buffers or reagents to mediate or measure AM-binding. The kit may also contain other suitably packaged reagents and materials needed for the binding protocol, including, for example, solid-phase matrices, standards, and instructions for conducting the test.

A further embodiment of the present invention is directed to in vitro screening and diagnostic methods for detecting or monitoring the presence of the AM/fH complex in biological samples, e.g., serum, plasma, or cell and tissue extracts or lysate. For use as screening and diagnostic reagents in the methods, antibodies that specifically recognize the AM/fH complex can be utilized according to well-established methods in the art. Such methods comprise the steps of:

i) contacting a sample suspected to contain altered levels of the AM/fH complex with an antibody specific for the complex under conditions in which a stable AM/fH-antibody association can form between the antibody and AM/fH complex in the sample; and ii) detecting any AM/fH-antibody association formed in step (i) using any suitable means known in the art, wherein the amount of the AM/fH-antibody association detected indicates the level of AM/fH complex in the sample.

Many immunoassay formats are known in the art, and the particular format used is determined by the desired application. An immunoassay may use, for example, a monoclonal antibody directed against a single AM/fH complex epitope or a combination of monoclonal antibodies directed against different epitopes of the AM/fH complex. Protocols may also, for example, use solid supports, or may involve immunoprecipitation. Examples of solid supports that can be used include, without limitation, nitrocellulose (e.g., in membrane or microtiter well form), polyvinyl chloride (e.g., in sheets or microtiter wells), polystyrene latex (e.g., in beads or microtiter plates), polyvinylidene fluoride (known as IMMUNOLON™), diazotized paper, nylon membranes, activated beads, and protein A beads. For example, Dynatech IMMUNOLON™ 1 or IMMUNOLON™ 2 microtiter plates or 0.23 inch polystyrene beads (Precision Plastic Ball) can be used.

Typically, immunoassays use either a labeled antibody or a labeled antigenic component (e.g., that competes with the antigen in the sample for binding to the antibody). Suitable labels include without limitation enzyme-based, fluorescent, chemiluminescent, radioactive, or dye molecules. Assays that amplify the signals from the probe are also known, such as, for example, those that utilize biotin and avidin, and enzyme-labeled immunoassays, such as ELISA assays.

Kits suitable for antibody-based diagnostic applications typically include one or more of the following components:

(i) Anti-AM/fH complex antibodies: The antibodies may be pre-labeled; alternatively, the antibody may be unlabeled and the ingredients for labeling may be included in the kit in separate containers, or a secondary, labeled antibody is provided; and (ii) Reaction components: The kit may also contain other suitably packaged reagents and materials needed for the particular immunoassay protocol, including solid-phase matrices, if applicable, and standards.

The kits may also include instructions for conducting the test. Furthermore, in preferred embodiments, the diagnostic kits are adaptable to high-throughput and/or automated operation.

Treatments Utilizing AM-Binding Proteins

Another embodiment of the present invention embraces treatments and therapeutic methods that comprise AM-binding proteins or peptides. Because AM-binding proteins or peptides are naturally occurring plasma components, they may be administered to an individual's circulatory system with minimal risk of immunological complications. Pharmaceutical compositions can be produced and employed in treatment protocols according to established methods depending on the disorder or disease to be treated (see, for example, P. D. Mayne, 1996, *Clinical Chemistry in Diagnosis and Treatment*, 6$^{th}$ ed., Oxford University Press, Oxford, England; Gilman et al., eds., 1990, *Goodman and Gilman's: The Pharmacological Basis of Therapeutics*, 8th ed., Pergamon Press; Avis et al., eds., 1993, *Pharmaceutical Dosage Forms: Parenteral Medications*, Dekker, N.Y.; and Lieberman et al., eds., 1990, *Pharmaceutical Dosage Forms: Disperse Systems*, Dekker, N.Y.).

In one embodiment of the present invention, peptides derived from factor H may be used as therapeutics. Such peptides can be produced by recombinant or synthetic techniques and then administered to tumor or cancer cells to inhibit the growth and/or proliferation of these cells. Non-limiting examples of cancer or tumor cells for use with the present invention include urinary bladder, urethral, renal, rectal, colon, small intestine, gastric, esophageal, salivary gland, gallbladder, liver, breast, vaginal, endometrial, ovarian, cervical, prostate, skin, lung, or brain cancer or tumor cells. It is noted that peptide-based treatments would be particularly advantageous, as peptides would not be expected to produce an undesirable immune response in the host, which may be observed during treatments using mouse monoclonal antibodies such as MoAb-G6 (Miller et al., 1996, supra).

In an alternative embodiment of the present invention, antibodies specifically bind to the AM/fH complex may be used as therapeutics. For example, anti-AM/fH antibodies can be formulated into a pharmaceutical composition and used to inhibit the growth or proliferation of cancer cells, in particular bladder cancer, breast cancer, and brain cancer cells.

It is noted that antibody-based therapeutics produced from non-human sources can cause an undesired immune response in human subjects. To minimize this problem, chimeric antibody derivatives can be produced. Chimeric antibodies combine a non-human animal variable region with a human constant region. Chimeric antibodies can be constructed according to methods known in the art (see Morrison et al., 1985, *Proc. Natl. Acad. Sci. USA* 81:6851; Takeda et al., 1985, *Nature* 314:452; U.S. Pat. No. 4,816,567; U.S. Pat. No. 4,816,397; European Patent Publication EP 171496; EP 0173494; United Kingdom Patent GB 2177096B). In addition, antibodies can be further "humanized" by any of the techniques known in the art, (e.g., Teng et al., 1983, *Proc. Natl. Acad. Sci. USA* 80:7308-7312; Kozbor et al., 1983, *Immunology Today* 4: 7279; Olsson et al., 1982, *Meth. Enzymol.* 92:3-16; International Patent Application WO92/06193; EP 0239400). Humanized antibodies can be also be obtained from commercial sources (e.g., Scotgen Limited, Middlesex, Great Britain). Immunotherapy with a humanized antibody may result in increased long-term effectiveness for the treatment of chronic disease situations or situations requiring repeated antibody treatments.

Pharmaceutical compositions may be produced as neutral or salt forms. Salts can be formed with many acids, including, but not limited to, hydrochloric, sulfuric, acetic, lactic, tartaric, malic and succinic acids. Compositions can take the form of solutions, suspensions, suppositories, tablets, pills, capsules, sustained release compounds, or powders. Such formulations can contain 10%-95% (w/w) of the active ingredient, preferably 25%-70% (w/w). Pharmaceutical preparations and compositions can also contain one or more physiologically acceptable carrier(s), excipient(s), diluent(s), disintegrant(s), lubricant(s), plasticizer(s), filler(s), colorant(s), dosage vehicle(s), absorption enhancer(s), stabilizer(s), or bacteriocide(s). The production and formulation of such compositions and preparations are carried out by methods known and practiced in the art.

Following the preparation of pharmaceutical compositions, they may be placed in appropriate containers and labeled for the treatment of indicated conditions. Such labeling can include amount, frequency, and method of administration. Preparations may be administered systemically by oral or parenteral routes. Non-limiting parenteral routes of administration include subcutaneous, intramuscular, intraperitoneal, intravenous, transdermal, inhalation, intranasal, intra-arterial, intrathecal, enteral, sublingual, or rectal.

A therapeutically effective amount of a pharmaceutical composition containing one or more AM-binding proteins or peptides is an amount sufficient to reduce, ameliorate, or eliminate a disease or disorder related to abnormal AM levels. An effective amount can be introduced in one administration or over repeated administrations to an individual being treated. Therapeutic administration can be followed by prophylactic administration, after treatment of the disease. A prophylactically effective amount is an amount effective to prevent disease and will depend upon the specific illness and subject. The therapeutically effective dose may be estimated initially, for example, either in cell culture assays or in animal models, usually mice, rats, rabbits, dogs, sheep, goats, pigs, or non-human primates. The animal model may also be used to determine the maximum tolerated dose and appropriate route of administration. Such information can then be used to determine useful doses and routes for administration in humans.

As an alternative approach, host cells can be genetically engineered to carry a nucleic acid encoding an AM-binding protein, or peptide fragment derived therefrom, and then introduced into a subject in need of modulation or reduction of AM levels. Following expression and production of the AM-binding protein by the cell, the so-produced AM-binding protein or peptide can act to bind AM and effect a disease state or disorder associated with abnormal levels of AM. Host cells may be genetically engineered by a variety of molecular techniques and methods known to those having skill in the art, for example, transfection, infection, or transduction. Transduction as used herein commonly refers to cells that have been genetically engineered to contain a foreign or heterologous gene via the introduction of a viral or non-viral vector into the cells. Transfection more commonly refers to cells that have been genetically engineered to contain a foreign gene harbored in a plasmid, or non-viral vector. Host cells can be transfected or transduced by different vectors and thus can serve as gene delivery vehicles to transfer the expressed products into muscle.

Although viral vectors are preferred for gene transfer therapies, cells can be genetically engineered to contain nucleic acid sequences encoding the desired gene product(s) by various methods known in the art. For example, cells can be genetically engineered by fusion, transfection, lipofection mediated by the use of liposomes, electroporation, precipitation with DEAE-Dextran or calcium phosphate, particle bombardment (biolistics) with nucleic acid-coated particles (e.g., gold particles), microinjection, or genetically engineered microorganisms (K. Yazawa et al, 2000, *Cancer Gene Ther.* 7:269-274). Vectors for introducing heterologous (i.e., foreign) nucleic acid (DNA or RNA) into muscle cells for the expression of active bioactive products are well known in the art. Such vectors possess a promoter sequence, preferably a promoter that is cell-specific and placed upstream of the sequence to be expressed. The vectors may also contain, optionally, one or more expressible marker genes for expression as an indication of successful transfection and expression of the nucleic acid sequences contained in the vector. In addition, vectors can be optimized to minimize undesired immunogenicity and maximize long-term expression of the desired gene product(s)(see Nabel, 1999, *Proc. Natl. Acad. Sci. USA* 96:324-326). Moreover, vectors can be chosen based on cell-type that is targeted for treatment. For example, vectors for the treatment of tumor or cancer cells have been described (P. L. Hallenbeck et al., 1999, *Hum. Gene Ther.* 10:1721-1733; T. Shibata et al., 2000, *Gene Ther.* 7:493-498; M. Puhlmann et al., 2000, *Cancer Gene Ther.* 7:66-73; N. Krauzewicz et al., 2000, *Adv. Exp. Med. Biol.* 465:73-82).

Illustrative examples of vehicles or vector constructs for transfection or infection of the host cells include replication-defective viral vectors, DNA virus or RNA virus (retrovirus) vectors, such as adenovirus, herpes simplex virus and adeno-associated viral vectors. Adeno-associated virus vectors are single stranded and allow the efficient delivery of multiple copies of nucleic acid to the cell's nucleus. Preferred are adenovirus vectors. The vectors will normally be substantially free of any prokaryotic DNA and may comprise a number of different functional nucleic acid sequences. An example of such functional sequences may be a DNA region comprising transcriptional and translational initiation and termination regulatory sequences, including promoters (e.g., strong promoters, inducible promoters, and the like) and enhancers which are active in the host cells. Also included as part of the functional sequences is an open reading frame (polynucleotide sequence) encoding a protein of interest. Flanking sequences may also be included for site-directed integration. In some situations, the 5'-flanking sequence will allow homologous recombination, thus changing the nature of the transcriptional initiation region, so as to provide for inducible or noninducible transcription to increase or decrease the level of transcription, as an example.

In general, the encoded and expressed AM-binding protein may be intracellular, i.e., retained in the cytoplasm, nucleus, or an organelle of a cell, or may be secreted by the cell. For secretion, the natural signal sequence present in the AM-binding protein may be retained. Alternately, an AM-binding protein or a fragment derived therefrom can be fused to a signal sequence to allow secretion of the fusion protein.

As previously mentioned, a marker may be present for selection of cells containing the vector construct. The marker may be an inducible or non-inducible gene and will generally allow for positive selection under induction, or without induction, respectively. Examples of marker genes include neomycin, dihydrofolate reductase, glutamine synthetase, and the like. The vector employed will generally also include an origin of replication and other genes that are necessary for replication in the host cells, as routinely employed by those having skill in the art. As an example, the replication system comprising the origin of replication and any proteins associated with replication encoded by a particular virus may be included as part of the construct. The replication system must be selected so that the genes encoding products necessary for replication do not ultimately transform the cells. Such replication systems are represented by replication-defective adenovirus (see G. Acsadi et al., 1994, *Hum. Mol. Genet.* 3:579-584) and by Epstein-Barr virus. Examples of replication defective vectors, particularly, retroviral vectors that are replication defective, are BAG, (see Price et al., 1987, *Proc. Natl. Acad. Sci. USA,* 84:156; Sanes et al., 1986, *EMBO J.,* 5:3133). It will be understood that the final construct may contain one or more genes of interest, for example, one or more genes encoding bioactive AM-binding proteins. In addition, cDNA, synthetically produced DNA, PCR amplified, or chromosomal DNA may be employed utilizing methods and protocols known and practiced by those having skill in the art.

According to one approach for gene therapy, a vector encoding an AM-binding protein is directly injected into the recipient cells (in vivo gene therapy). Alternatively, cells from the intended recipients are explanted, genetically modified to encode an AM-binding protein, and reimplanted into the donor (ex vivo gene therapy). An ex vivo approach provides the advantage of efficient viral gene transfer, which is superior to in vivo gene transfer approaches. In accordance with ex vivo gene therapy, the host cells are first infected with engineered viral vectors directing the expression of at least one AM-binding protein, suspended in a physiologically acceptable carrier or excipient such as saline or phosphate buffered saline, and the like, and then administered to the host. The desired AM-binding protein is expressed by the injected cells, which thus introduce the AM-binding protein into the host. The introduced AM-binding protein can thereby be utilized to treat or ameliorate a disorder that is related to altered circulating levels of AM.

EXAMPLES

The examples as described herein are intended to further illustrate the present invention and are not intended to limit the invention.

Example 1

Non-radioactive labeling of AM was accomplished by conjugating synthetic AM comprising amino acids 1-52 (Phoenix Pharmaceuticals, Inc., Mountainview, Calif.) with succinimidyl esters linked to biotin (Pierce Chemical Co., Rockford, Ill.), fluorescein (Molecular Probes, Inc., Eugene, Oreg.), or dinitrophenol (DNP; Molecular Probes, Inc.). Briefly, 100 μg of AM (16 μM) was dissolved in 1 ml of 50 mM sodium bicarbonate, pH 8.5, and the succinimidyl ester was added to yield a final molar concentration of 10:1 (linker:AM). The mixture was incubated with slow agitation for 1 hr at room temperature and the reaction was terminated by the addition of 0.1 M ethanolamine followed by another incubation for 1 hr. Unincorporated ligand was removed by extracting the AM using reverse phase SEP-PAK® C-18 solid-phase extraction cartridges (Waters, Milford, Mass.) and eluting the sample with acidic-isopropanol. The extract was lyophilized and reconstituted in 1 ml of TBS (0.05 M Tris-HCl, 0.15 M NaCl), 0.1% alkali-treated casein (ATC), 0.1% TWEEN® 20 nonionic detergent, and 0.05% TRITON® X-100 nonionic detergent, pH 7.4. Labeled AM was stored at 4° C. for as long as 3 months without significant loss of activity.

Example 2

AM-binding proteins were identified using an in vitro screening method. Total proteins derived from human plasma (2 μl) were electrophoretically fractionated on 3-8% Tris-acetate gel (Novex, San Diego, Calif.) under non-reducing conditions. For the ligand blotting experiment, the proteins were transferred to a 0.2 mm nitrocellulose membrane that was incubated for 15 mm with 1% Nonidet P-40 (NP-40). Non-specific binding was further blocked with a 2 hr incubation in TBS containing 0.1% ATC. Incubations with 70 nM AM labeled with biotin, fluorescein, or DNP were carried out overnight at 4° C. in blocking buffer containing 0.1% TWEEN® 20 nonionic detergent. For biotin detection, the ligand blot was incubated with an avidin-biotin-peroxidase complex and the AEC reagent (Vector Laboratories, Inc., Burlingame, Calif.). For fluorescein and DNP, the ligand blots were incubated 1 hr at room temperature with rabbit anti-fluorescein or anti-DNP IgG, respectively, (1:1000 in incubation buffer; Molecular Probes, Inc.). Anti-rabbit antibody labeled with alkaline phosphatase (1:2000; Dako Corporation, Carpenteira, Calif.) was added for 0.5 hr, and the blot was developed using 4-nitro blue tetrazolium chloride/5-bromo-4-chloro-3-indolyl phosphate (NBT/BCIP) as the color-substrate solution (Roche Molecular Biochemicals, Indianapolis, Ind.). Ligand blotting was used to detect AMBP-1, a 120 kD protein subsequently identified as human complement factor H. FIG. 1.

Example 3

Figure 2:
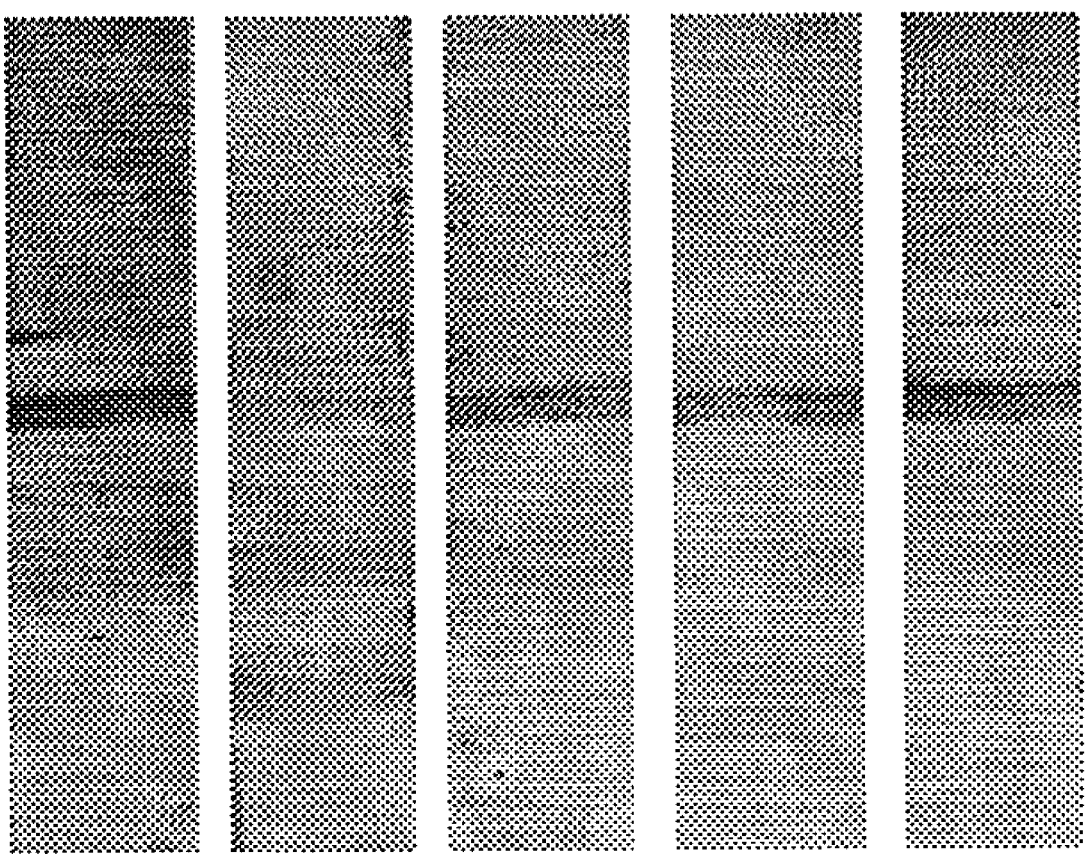
FIG. 2 illustrates the results of a representative competition binding assay to assess the specificity of binding between fluorescein-labeled AM and AMBP-1 (factor H). Lane 1: no competitor added; Lane 2: AM added; Lane 3: insulin-like growth factor (IGF-1) added; Lane 4: proadrenomedullin N-terminal 20 peptide (PAMP) added; Lane 5: insulin added. "f-AM+" indicates fluorescein-labeled AM. The band represents the AM/AMBP-1 (AM/fH) complex that is unaffected by the presence of competitor peptides.
Figure 3:
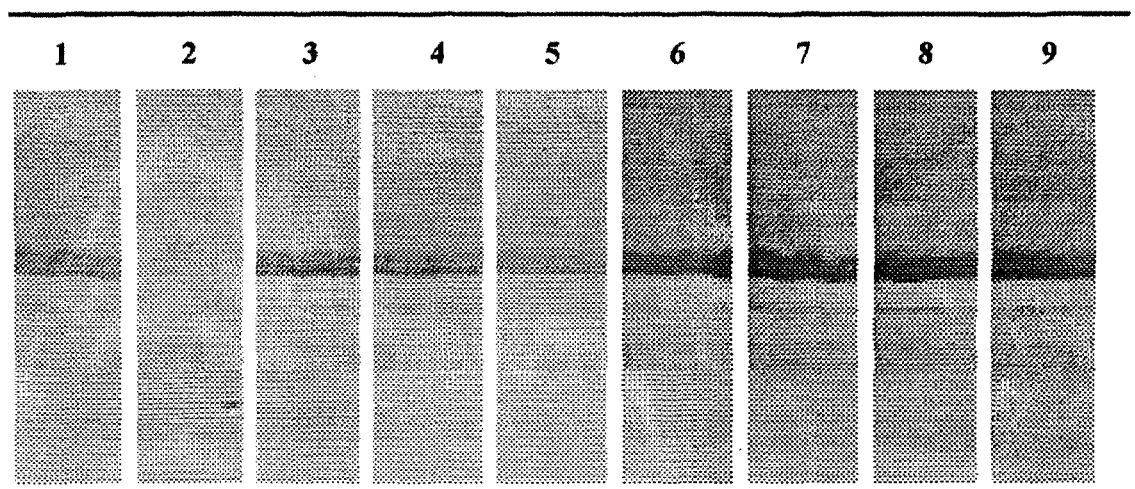
FIG. 3 illustrates the results of a representative competition binding assay to assess the specificity of binding between fluorescein-labeled AM and AMBP-1 (factor H). Lane 1: no competitor added; Lane 2: full-length AM added; Lane 3: $AM_{1-12}$ added; Lane 4: $AM_{16-21}$, added; Lane 5: $AM_{22-52}$ added; Lane 6: $AM_{13-52}$ added; Lane 7: $AM_{34-52}$ added; Lane 8: calcitonin gene-related peptides (CGRP) added; Lane 9: amylin peptides added. "f-AM+" indicates fluorescein-labeled AM. The band represents the AM/AMBP-1 (factor H) complex that is unaffected by presence of competitor peptides.

Competition of full-length AM binding to AM-binding proteins was tested by pre-incubating a membrane having plasma derived proteins bound thereto with 7 μM of unlabeled peptides; e.g., CGRP, amylin, insulin, IGF-1, PAMP, or AM truncated polypeptides ($AM_{1-12}$, $AM_{16-21}$, $AM_{22-52}$, $AM_{13-52}$, $AM_{34-52}$) for 6 hr at 4° C. Following this preincubation, labeled full-length AM was introduced and incubated overnight at 4° C. Competition studies indicated that only full-length AM was able to dissociate the AM/AMBP-1 (AM/fH) complex. FIGS. 2 and 3.

Example 4

According to the present invention, a plasma-derived polypeptide that showed specific binding to full-length AM was determined to be factor H. Prior to the formal identification of this AM-binding protein as factor H, it was termed "AM-binding protein" or "AMBP-1" by the present inventors. Isolated and purified AMBP-1 was found to have a molecular weight of approximately 120 kD when subjected to SDS-PAGE under nonreducing conditions.

AMBP-1 was purified to homogeneity using HPLC (FIG. 4A) followed by SDS-PAGE under non-reducing conditions (FIGS. 4B and 4C). Preparative reverse phase high performance liquid chromatography (HPLC) was performed using a Delta Pak C18-300 Å column (30 mm×30 cm, Waters, Tokyo, Japan) and the SYSTEM® modular chromatography system (Beckman Instruments Inc., Fullerton, Calif.). Two and one-half milliliters of human plasma were mixed with an equal volume of 10% acetonitrile with 0.2% trifluoroacetic acid, processed through a 0.2 μm filter and loaded onto the column. After 5 mm with 0.1% trifluoroacetic acid in 5% acetonitrile, the column was eluted with a linear gradient of acetonitrile containing 0.075% trifluoroacetic acid from 5% to 60% at a flow rate of 12 ml/min over 60 mm. Each fraction (12 ml) was collected, freeze-dried and dissolved in 0.3 ml of TBS 0.1% TWEEN® 20 nonionic detergent. Fractions were separated by SDS-PAGE and then stained with Coomassie Blue (FIG. 4B) or tested for the presence of AMBP-1 using the non-radioactive ligand blotting technique (FIG. 4C).

AMBP-1 was identified in fractions number 48-51, and was found to be concentrated in fractions number 48-49 (FIGS. 4B and 4C). Fraction number 49 was electophoresed by preparative SDS-PAGE and electroblotted to PVDF. The AMBP-1 band was identified by Coomassie brilliant blue R™ staining, excised, and used for amino acid analysis and amino acid sequence analysis.

Example 5

Amino acid analysis was performed by The Protein/DNA Technology Center at the Rockefeller University, New York. HPLC (NovaPak C18 30 cm-column) with the Waters Pico-Tag Workstation and a two pump gradient system (model 510) equipped with a model 490 UV multiwavelength detector were used as previously described (F. Gharahdaghi et al., 1992, in *Techniques in Protein Chemistry III* pp. Academic Press, Inc., San Diego, Calif., pp 249-260). The results of the AMBP-1 amino acid analysis are shown below in Table 1 in which % AMBP-1 and % fH are compared.

TABLE 1

Amino acid composition of AMBP-1 and factor H

| | % of total amino acid composition[a] | |
|---|---|---|
| | AMBP-1 | fH[c] |
| Asx[b] | 12.7 | 9.4 |
| Glx[b] | 13.2 | 12.2 |
| Ser | 8.1 | 8.2 |
| Gly | 8.3 | 8.5 |
| His | 2.6 | 2.5 |
| Arg | 4.4 | 4.9 |
| Thr | 6.4 | 6.6 |
| Ala | 3.4 | 3.3 |
| Pro | 7.8 | 8.0 |
| Tyr | 5.8 | 6.1 |
| Val | 6.4 | 5.5 |
| Met | 0.9 | 1.7 |
| Ile | 5.8 | 5.9 |
| Leu | 5.0 | 5.0 |
| Phe | 2.8 | 2.7 |
| Lys | 6.4 | 7.0 |

[a]Since tryptophan and cysteine are destroyed by the hydrolysis of the protein in 6 M HCl, the calculated composition of factor H corresponds to the 18 amino acids recovered.
[b]The combined values for asparagine and aspartic acid, and glutamine and glutamic acid are expressed as Asx and Glx, respectively.
[c]The amino acid composition of factor H was obtained from the protein sequence database SWISS-PROT (accession number: P08603).

Although the percentage of methionine determined for AMBP-1 was about one-half of the percentage of methionine predicted for factor H, the recovery of methionine from the control protein (bovine serum albumin) was also about half of the expected value. The amino acid composition profile was used to search a sequence database. This search indicated that the amino acid composition profile shared the highest degree of similarity to human complement factor H.

The N-terminal sequence analysis was performed by the Biotechnology Resource Laboratory, Protein Sequencing and Peptide Synthesis Facility, Medical University of South Carolina, Charleston, S.C. The sample was subjected to automated Edman degradation using a PE Biosystems Procise 494 Protein Sequencer and a PE Biosystems cLC Microblotter 173, using standard cycles and reagents (P. Edman and G. Begg, 1967, *Eur J. Biochem.* 1:80-91; M. W. Hunkapiller et al., 1983 *Methods Enzymol.* 91:399-413).

The Edman degradation results for AMBP-1 were analyzed using the ExPASy Molecular Biology Server protein database. This analysis indicated that the AMBP-1 amino acid sequence showed an 80% homology match with human complement factor H. Secondary amino acids were attributed to autolytic cleavage of the polypeptide. The sequence of the 15 amino acid N-terminus of AMBP-1 was identical to the N-terminus of factor H with the exception of the threonine in position 12.

For Mass Spectrometry analysis, AMBP-1 was run on a SDS-PAGE gel under reducing conditions (5% β-mercaptoethanol). The gel was stained with Coomassie Blue and the AMBP-1 band was excised. In-gel protein digestion and peptide extraction were performed as previously described (J. Rosenfeld et al., 1992, *Anal. Biochem.* 203:173-179). One-tenth of the extracted protein digest was analyzed by MALDI-TOF on a PerSeptive Voyager-DE STR (PE Biosystems, Foster City, Calif.) prior to LC/MS. The instrument was operated in reflector mode with the accelerating voltage set to 20000, the laser energy to 2350, the guide wire voltage to 0.05%, and the grid voltage to 95%. The mirror ratio was set to 1:110.

The remainder of the extracted protein digest was injected onto a 0.3×100 mm, 5 μm BASIC® C18 solid-phase extraction column (Keystone Scientific, Bellafonte, Pa.) which had been equilibrated with 10% buffer B in buffer A (buffer A: water with 0.1% formic acid; buffer B: acetonitrile with 10% 1-propanol and 0.1% formic acid). Peptide elution was carried out using a linear gradient progressing from 10% to 60% buffer B over 60 mm (Shimadzu Sci. LC10AD/VP pumps and LC10A controller). The eluting peptides were detected by a Finnigan LCQ Mass Spectrometer (ThermoQuest, Finnigan MAT Division, Piscataway, N.J.). Peptide sequence data was obtained from the eluting peptides by MS/MS on those ions exceeding a preset threshold of $5 \times 10^4$ ions. The operating parameters were as follows: sheath gas flow set to 32, auxiliary gas flow set to 1, spray voltage set to 4.5 kV, capillary temperature set to 200° C., capillary voltage set to 8.0 volts, and tube lens offset set to −20 volts.

Example 6

The isolated AM-binding plasma protein termed AMBP-1 was compared with factor H, based on apparent molecular weight, glycosylation, AM-binding, and recognition by anti-factor H antibodies.

Human factor H had been characterized as a glycoprotein having a calculated molecular weight of approximately 150 kD when run under reducing conditions (in the presence of 5% 2-mercaptoethanol)(R. B. Sim et al., 1982, *Biochem. J.* 205: 285-93; P. F. Zipfel et al., 1999, *Mol. Immunol.* 36:241-8). It was demonstrated that AMBP-1 was glycosylated using the GelCode® Glycoprotein Staining Kit (Pierce Chemical Co.), and that AMBP-1 migrated at a molecular weight of approximately 150 kD under reducing conditions. FIG. 5A.

Additionally, $^{125}$I-labeled AM (Phoenix Pharmaceuticals, Inc.) exhibited high-affinity binding to immobilized commercially produced factor H ($10^{-8}$ M to $10^{-9}$ M)(FIG. 5C), and Western blot analysis indicated that commercially produced antibodies to factor H (Quidel Corporation, San Diego, Calif.) recognized plasma-purified AMBP-1 (FIG. 5D). For Western blot analysis, proteins were electrophoretically separated on a 3-8% Tris-acetate (for factor H) or a 4-12% Bis-Tris gel (for AM) under non-reducing conditions, transferred to a 0.2 μm nitrocellulose membrane, and blocked with 5% non-fat dry milk in PBS. Following the blocking step, the membrane was incubated with 1:2000 anti-factor H rabbit antibody (Quidel, San Diego, Calif.) or 1:4000 anti-AM rabbit antibody (Martinez et al., 1996, supra), and developed using the ECL+Plus Western Blot Detection System (Amersham Pharmacia Biotech, Piscataway, N.J.).

Example 7

To analyze the AM/fH interaction, the purified AMBP-1 (factor H) fraction (#48) was analyzed using the non-radioactive ligand-blotting assay (Example 1). After incubation with fluorescein-labeled AM, the membrane was incubated under different conditions, including PBS; PBS pH 11.5; PBS pH 2.5; 4M NaCl; 4M NaCl pH 11.5; NaCl pH 2.5; 1% SDS; 3M Urea; 3M Guanidine-HCl; 3M NaSCN; 50% ethylene glycol pH 11.5; 50% ethylene glycol; 1% β-mercaptoethanol. The assay was then developed as described (Example 1). FIG. 6A.

Alternatively, the AM/fH interaction was analyzed using a multi-well assay. In accordance with this assay, a 96-well polyvinylchloride (PVC) plate was coated with factor H (5 ng/well, Sigma, St. Louis, Mo.). The plate was blocked with a solution containing TBS, 0.1% ATC, and 0.1% TWEEN® 20 nonionic detergent, and then incubated with fluorescein-labeled AM (50 nM) for 2 hr. Prior to the development of the assay, the wells were incubated for various time periods with PBS or 3M NaSCN pH 7.4. Following this, the plate was washed and incubated with anti-fluorescein polyclonal antibody (1:1000, Molecular Probes) and $^{125}$I-Protein A (Amersham Pharmacia Biotech). Radioactivity was determined using a gamma counter. FIG. 6B.

Example 8

To determine factor H and AM distribution following C18 extraction, 1 ml of human plasma was processed through a SEP-PAK® C18 solid-phase extraction cartridge. The bound and unbound fractions were tested for the presence of factor H by Western blot analysis (FIG. 7A). Alternatively, bound and unbound fractions were tested for the presence of AM by immunoprecipitation of AM followed by Western blot analysis (FIG. 7B). Immunoprecipitation of AM was performed as follows: a 3 ml sample was incubated for 1 hr at 4° C. with 1 ml of Protein A-agarose (Life Technologies, Rockville, Md.) containing 1 μM final concentration of each of the following protease inhibitors: PEFABLOC® protease inhibitor (Centerchem Inc., Stamford, Conn.), Bestatin, and Phosphoramidon (Sigma). The sample was then centrifuged and the supernatant was removed to another tube. The supernatant was incubated with 80 μl of rabbit anti-AM antibodies (Martinez et al., 1996, supra) or rabbit preimmune serum for 1 hr at 4° C. The antibody mixture was incubated with 80 μl of Protein A-agarose for 30 mm. Following this, the immunoprecipitate was collected by centrifugation and the pellet was extensively washed with TBS with 0.1% TRITON® X-100 nonionic detergent. The pellet was then resuspended in 100 μl of LDS sample buffer (Novex) and boiled before the Western blot analysis.

For the standard RIA protocol, plasma extraction was performed using reverse-phase SEP-PAK® C18 solid-phase extraction cartridges (Waters) as previously reported (L. K. Lewis et al., 1998, *Clin. Chem.* 44: 571-577; A. Martinez et al., 1999, *Peptides* 20:1471-1478). Briefly, cartridges were activated with 80% methanol and washed with 0.9% NaCl. Plasma samples were mixed with an equal volume of phosphate buffer saline containing 0.1% ATC and 0.1% TRITON® X-100 nonionic detergent, pH 7.4. Samples were applied to the columns and, after washing twice with 0.9% NaCl, AM was eluted with 80% isopropanol containing 125 mM HCl. Extracts were freeze-dried to remove the organic solvent. Concentrations of AM in the extracts were measured by radioimmunoassay as previously described (Martinez et al., 1999, supra).

For the NaSCN-modified RIA protocol, 1 ml of plasma was pre-incubated with an equal volume of 6M NaSCN in PBS with 0.1% ATC and 0.1% TRITON® X-100 nonionic detergent pH 7.4 for 10 mm at room temperature. Following this, plasma was extracted through the C18 cartridges and AM levels were quantified. The AM levels measured using NaSCN-modified RIA were twofold higher than those obtained with the standard RIA. Mean and standard deviation values of the three donors were 23.0±4.8 pg/ml (standard RIA) 54.3.±8.6 pg/ml (NaSCN-modified RIA). Identical results were obtained using a longer NaSCN pre-incubation step (16 hr at 4° C.). Using the NaSCN-modified RIA, recovery of unlabeled AM added to human plasma (200 pg) was 93.9±18.7% (n=3), whereas recovery of $^{125}$I-AM was 82.7%±4.4% (n=6). The parallel trajectory of the competitive binding curves indicated that the increase in AM levels detected following NaSCN treatment was not attributable to an artifact. FIG. 8.

Example 9

For the cAMP assay, Rat-2 fibroblasts were grown in RPMI 1640 containing 10% fetal bovine serum (Life Technologies). Cells were seeded into 24-well plates at $2 \times 10^5$ cells/well and incubated for 48 hr at 37° C. in 5% $CO_2$. Cells were preincubated in TIS medium (RPMI 1640 plus 10 µg/ml transferrin, 10 µg/ml insulin and 50 nM sodium selenite) for 15 min. Following this, cells were treated for 5 min with AM (Bachem, King of Prussia, Pa.) and/or factor H (Sigma) in 250 µl of TIS medium containing 1% BSA, 1 mg/ml bacitracin and 100 µM isobutylmethylxanthine. The reaction was terminated by adding an equal volume of ice-cold ethanol. Cyclic AMP was measured using the Biotrac cAMP RIA (Amersham Pharmacia Biotech). FIG. 9A.

Antimicrobial activity was measured using *E. coli* cells (ATCC 35218, Gaithersburg, Md.) and a radial diffusion assay as previously described (R. I. Lehrer et al., 1991, *J. Immunol. Methods* 137:167-173). Briefly, bacteria were incorporated into a thin underlay gel that contained 1% agarose, 2 mM HEPES pH 7.2, and 0.3 mg/ml of trypticase soy broth powder. After polymerization of the gel, small wells (10 µl capacity) were carved in the agar. Test substances were added and allowed to diffuse for 3 hr at 37° C. A 10 ml overlay gel composed of 1% agarose and 6% trypticase soy broth powder was poured on top of the previous gel and the plates were incubated for 16 hr at 37° C. The diameters of the inhibition halos were measured to the nearest 0.1 mm and, after subtracting the diameter of the well, were expressed on inhibition units (10 units=1 mm). The minimal inhibitory concentration (MIC) was estimated by performing a linear regression and determining the x-intercepts. FIG. 9B.

For statistical calculations, MIC values were analyzed by the Student's t test, cAMP values were analyzed with a one-way analysis of variance (ANOVA) and the Tukey's test, and $P<0.05$ was considered significant.

To measure the cofactor activity of factor H, C3b (28 pmols) was incubated with factor I (0.16 pmols) and factor H (0.16 pmols) in the presence or absence of AM and related peptides for 24 hr at 37° C. in a final volume of 50 µl of PBS. Samples were fractionated by SDS-PAGE using 4-12% Tris-Bis gels (Novex) under reducing conditions, and stained with Coomassie Blue. C3b and factor I were purchased from Advanced Research Technologies (San Diego, Calif.). FIGS. 10A and 10B.

Example 10

Northern blot analysis was used to determine the expression of factor H (4.3 kb) and FHL-1 (1.8 kb) message in various human tumor cell lines. A $^{32}P$ labeled 854 bp PCR product was used as a probe to detect Factor H and FHL-1 mRNA in the same Northern blot. The sequence information for factor H and FHL-1 was obtained from GenBank Accession Nos. Y00716 (factor H) and X07523 (FHL-1). To obtain the PCR product/probe, PCR was performed of using a sense primer corresponding to positions 555-576 of factor H (5'-CAATGGAACCAGATCGGGATTA (SEQ ID NO:1)) and the antisense primer corresponding to positions 1378-1408 of factor H (5'-GACACGGATGCATCTGGGAGTA (SEQ ID NO:2)). Total RNA from human liver was reverse transcribed to cDNA and used as template. The northern gel was loaded with 15 µg total RNA per well (carcinoma samples), or 5 µg total RNA per well (normal skin sample). To confirm equivalent amounts of total RNA loaded in each well, the gel was stained with ethidium bromide and illuminated with UV. FIG. 11.

Example 11

For Immunohistochemical analysis, 6 male albino Wistar rats were euthanized with $CO_2$, and perfused with the fixative (4% paraformaldehyde) through a heart canula. The pancreas from each rat was extracted and immersed in the same fixative for an additional period of 5 h. After dehydration, the tissues were embedded in paraffin and sectioned according to routine procedures.

Two commercially available polyclonal antibodies against human factor H were used in conjunction with an avidin-biotinylated peroxidase detection kit (Dakopatts, Glostrup, Denmark). The antibodies were goat anti human factor H (Quidel, San Diego, Calif.) and rabbit anti human factor H (Serotec, Raleigh, N.C.). To ensure the specificity of the signal, liquid-phase and solid-phase absorption controls were performed with purified human factor H (Sigma, St. Louis, Mich.). For liquid-phase absorptions, 10 nmols of factor H were added per ml of optimally diluted antibody for 2 hr at room temperature before incubating the tissue sections. For solid-phase absorptions, factor H was linked to Ultralink Biosupport Medium (Pierce, Rockford, Ill.), the optimally diluted antibody was exposed to it for 2 hr at room temperature, and the immune complexes removed by centrifugation. FIGS. 12A-12C.

Anti-factor H antibodies were then purified by affinity chromatography column containing solid-phased factor H. Briefly, 1 mg of factor H was covalently coupled to 250 mg ULTARLINK® polyacrylamide resin Biosupport Medium (Pierce) following manufacturer's instructions. Rabbit anti-factor H serum (250 µl) was incubated with the resin for 16 hr in 5 ml of PBS at 4° C. Following this, the resin was packed in a column and washed intensively with PBS. The bound antibody was eluted with 0.1 M citric acid, pH 3.3. The eluate was neutralized with 1 M sodium phosphate pH 8.0, and the buffer changed to PBS by ultracentrifugation in CENTRICON® 50 centrifugal filtration columns (Amicon, Millipore Corporation, Bedford, Mass.). Solid-phase absorption of this affinity-purified antibody resulted in a successful quenching of the staining. FIG. 12D.

Example 12

Triple immunofluorescence labeling and confocal microscopy was performed as follows. Non-specific binding was blocked with donkey normal serum (Jackson Immunoresearch Laboratories, West Grove, Pa.). Paraffin sections were incubated in a mixture of three primary antibodies, including: i) Guinea-pig anti bovine insulin antibodies (1:2,000)(Jackson Immunoreasearch Labs.); ii) affinity purified rabbit anti human factor H antibodies (1:200) described above; and iii) one of the following monoclonal antibodies: anti-somatostatin antibodies (1:10,000), anti-glucagon antibodies (1:1,000), or anti-rat pancreatic polypeptide antibodies (1:500)(all obtained from CURE (UCLA, CA)).

Following overnight incubation at 4° C., the sections were incubated for 1 hr with a mixture of secondary antibodies, including Cy5-conjugated donkey anti-Guinea-pig antibodies (Jackson Immunoresearch Laboratories), Bodipy-conjugated anti-mouse antibodies (Molecular Probes, Eugene, Oreg.), and biotinylated goat anti-rabbit (Dakopatts), all at a final concentration of 1:200. The sections were then incubated with lissamine rhodamine streptavidin (1:200) (Jackson Immunoresearch Laboratories) for 1 h. After extensive washing, the slides were mounted in SLOWFADE® fluorescence antifade reagent solution (Molecular Probes) and observed with a Zeiss Laser Scanning microscope 510, equipped with four lasers. FIGS. 13A-13L.

Example 13

Figure 14C:
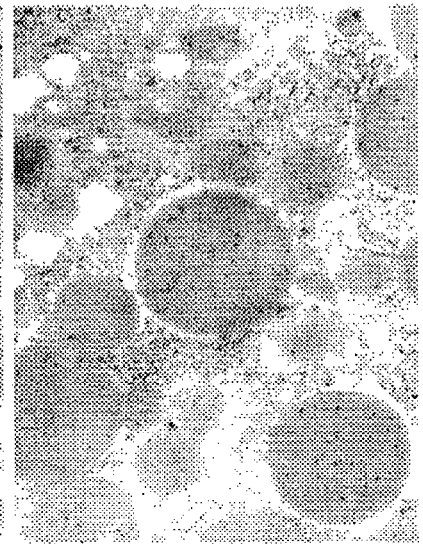

For immunoelectron micrographic studies, 4 male albino Wistar rats were euthanized and pancreatic-extraction was performed as previously described. Small fragments of each pancreas were fixed in 1% glutaraldehyde plus 2% paraformaldehyde in 0.1 M cacodylate buffer, pH 7.2 at 4° C. for 2 h. The fragments were then dehydrated, and embedded in the epoxy resin, TAAB-812 (TAAB Labs. England). Ultrathin sections (60-80 nm) were placed on nickel grids, etched for 5 min in 3% $H_2O_2$, and subjected to double immunogold staining (J. López et al., 1999, *Gen. Comp. Endocrinol.* 115:309-322). Briefly, the sections were incubated in a mixture of both primary antibodies (anti-insulin and anti-factor H) at 4° C. overnight. On the following day, the sections were incubated with secondary antibodies conjugated to gold particles (E-Y Laboratories Inc., San Mateo, Calif.). The large gold particles (20 nm in diameter) localized the anti-insulin antibody, while the small gold particles (10 nm) localized the anti-factor H antibody. The grids were washed extensively and stained with 5% aqueous uranyl acetate for 15 min, and with lead hydroxide for 7 min. The stained sections were analyzed using a JEOL-1010 electron microscope. FIGS. 14A-14C.

Example 14

Figure 15B:
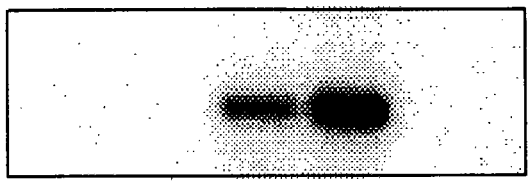
FIG. 15 illustrates RT-PCR analysis to determine factor H expression in mouse liver and pancreas.

The expression of complement factor H in the pancreas was confirmed by RT-PCR analysis. Primers were designed using the sequence of the mouse gene (GenBank accession number M12660): sense primer (1877-1896) 5'-TTGGAAT-TCTCCTGCCATTC-3' (SEQ ID NO:3) and antisense primer (2644-2663) 5'-ACCTTCCATCTTTGCACACC-3' (SEQ ID NO:4). Total RNA was prepared from the liver and pancreas of two Balb/c mice, and reverse transcription was performed using the SUPERSCRIPT® reverse transcriptase Preamplification System (Life Technologies, Gaithersburg, Md.). PCR amplification was performed with ELONGASE® DNA polymerase enzyme mixture (Life Technologies) for 35 cycles, with an annealing temperature of 57° C. The PCR products were cloned into pCR-Blunt II-TOPO (Invitrogen, Carlsbad, Calif.) and sequenced by Lark Technologies (Houston, Tex.). RT-PCR results were confirmed by Southern blot analysis. FIGS. 15A and 15B.

Example 15

Pancreatic islets were isolated from 12 rats as previously described (A. Martínez et al., 2000, *Endocrinology* 141:406-411). Briefly, the heart of each rat was perfused with Hank's balanced salt solution (Sigma) to remove blood from pancreatic vessels. A small canula was inserted into the common biliary duct while the coledoco was sealed. Twenty to twenty-five milliliters of 0.4 mg/ml collagenase XI (Sigma) in Hank's solution was pumped through the canula until the pancreas was fully inflated. The pancreas was removed and incubated at 37° C. for 20 min. Following this, 20 ml of ice-cold Hank's solution was added and the pancreas dissociated by vigorous vortexing. After several washes, the islets were collected and distributed into 24 well plates using a dissecting microscope, with approximately 70 islets per well.

Freshly isolated islets were incubated in RPMI-1640 (Life Technologies) containing 5.6 mM glucose for 45 min at 37° C. The supernatant was isolated for analysis and the islets incubated in RPMI-1640 containing 20.6 mM glucose plus the potential secretagoges (AM and/or factor H) for another 45 min. The medium was isolated for analysis and the islets were dissolved in ice-cold ethanol to measure cAMP production. Insulin and cAMP were measured by radioimmunoassay with commercial kits (Amersham, Arlington Heights, Ill.), according to the manufacturer's directions. FIGS. 16A and 16B.

Insulin release was expressed as the ratio between the contents in the high glucose medium divided by the amount in the low glucose medium to allow for variations in the number of secreting cells and/or their secretory efficiency. Graphs represent the mean and standard deviation of three wells per treatment. These experiments were performed three times with comparable results. Two-tailed Student's test was performed to determine statistical significance. P values <0.05 were considered statistically significant.

Example 16

Experiments were carried out utilizing radiolabeled AM as ligand. Radioligand blotting assays were performed to establish that AM-BPs were present in the plasma of several animal species and to further determine the specificity of binding between AM and the plasma-derived AM-binding protein on a solid membrane such as nitrocellulose (see T. H. Elsasser et al., 1999, *Endocrinology* 140:4908-4911).

Blood sera and plasma were collected and pooled from calves (4-5 months old), pigs (6-7 months old), goats (2 years old), dogs (6-8 years old), mice (4-6 months old), chickens (6-8 weeks old), and human (adult male) and were aliquoted and stored at −20° C. until needed. Initial chromatographic determination of high molecular weight plasma proteins capable of binding recombinant human $^{125}$I-AM (Phoenix Pharmaceuticals, Mountain View, Calif.) was accomplished using a 0.7×30 cm column of SEPHADEX® G-50 superfine cross-linked dextran gel(Pharmacia LKB, Uppsala, Sweden) equilibrated with 50 mM phosphate, 50 mM disodium EDTA, 135 mM NaCl, 0.1% TWEEN® 20 nonionic detergent and 0.125% alkaline-hydrolyzed casein (AHC; 7), pH 7.2. For gel chromatography studies of solution binding of $^{125}$I-AM to plasma proteins, bovine plasma (0.1 or 0.3 ml) was mixed with 50,000 cpm of $^{125}$I-AM, incubated at 4° C. overnight and applied to the column with phosphate buffered saline in a final volume of 0.5 ml. One milliliter fractions were collected using gravity flow and the radioactivity was quantified.

Further detection and characterization of AM-BPs were performed using radioligand blotting procedures similar to those described for IGF binding proteins in plasma (P. Hossenlopp et al., 1986, *Anal. Biochem.* 154:138-146). Briefly, plasma or serum from the ten species was diluted 1:5 with water and further mixed 1:2 with SDS Tris-glycineglycerol loading buffer and incubated for 10 min at 70° C. Plasma or serum volumes equivalent to 1.5 µl were loaded onto 10% acrylamide gels under non-reducing conditions. Proteins were separated at 115 v for 0.5 hr and transferred to 0.2 µm nitrocellulose using a semi-moist transfer (Bio-Rad Hercules, Calif.) at 18 v for 42 min. Molecular weight markers (29 kD, 43 kD, 66 kD, 78 kD, and 116 kD) were added to complementary lanes on each gel to assess the relative sizes of the resolved proteins.

Nitrocellulose blots were incubated for 15 min with 1.5% NP-40 (Sigma, St. Louis, Mo.). Nonspecific binding was further blocked with a 4 hr incubation of the nitrocellulose in phosphate buffered saline containing either 1% BSA (RIA Grade, SIGMA, St. Louis, Mo.) or 1% AHC. Incubations with radiolabeled recombinant human $^{125}$I-AM were performed overnight at room temperature with agitation, with 80,000 CPM $^{125}$I-hAM per 5 ml protein blocking matrix. The next morning, the nitrocellulose was washed 10 min with 0.2% NP-40, and further washed 4 times for 15 min per wash with phosphate buffered saline. Following air drying, the nitrocellulose was loaded into a phosphoimaging cassette (Molecular Dynamics, Sunnyvale, Calif.) overnight for analysis of resolved band images. Additional characterization of the banding patterns was accomplished by autoradiography of the blots on Kodak AR-5 film with a 4-day exposure at −80° C. Removal of apparent binding proteins from plasma was accomplished using the C-18 reverse-phase Sep-Pak® RIA preparatory technique (A. Martínez et al., 1997, *Endocrinology* 138:5597-5604). FIG. 17.

Competitive displacement of $^{125}$I-AM from separated proteins on nitrocellulose ligand blot strips was performed to assess the specificity of the AM binding to the AM-binding protein. Blot strips were incubated in buffer containing 0.1% AHC, $^{125}$I-AM, and concentrations of recombinant human AM ranging from $10^{-10}$ to $10^{-6}$ M. The intensity of the band images was resolved by phosphoimaging densitometry. Additional aspects of AM specificity for the binding protein(s) were assessed by co-incubating $^{125}$I-AM overnight with authentic $AM_{1-52}$ ($10^{-6}$M) or $AM_{1-12}$, $AM_{13-52}$, $AM_{34-52}$ peptide fragments, or amylin, CGRP or insulin used at $10^{-5}$M. The results showed a linear competitive displacement of $^{125}$I-AM from the AMBPs in the presence of increasing concentrations of non-labeled synthetic AM (Elsasser et al., 1999, supra).

Example 17

A comparison of $^{125}$I-AM blot binding patterns in bovine plasmas from healthy and parasitized calves was used to determine whether plasma AM-BP content was affected by the health status of a subject (Elsasser et al., 1999, supra). Nitrocellulose transfer blots of plasma proteins from normal healthy 4 month old calves (n=3) and calves infected with a vascular endothelial-resident parasite (*Sarcocystis cruzi*), (n=4), were probed with $^{125}$I-AM. Plasma from infected calves was obtained on day 30 post oral inoculation (250,000 oocysts) at the peak of expression of clinical signs of the acute phase response associated with the eruption of schizonts from the endothelium (T. H. Elsasser et al., 1988, *J. Endocrinol.* 116:191-200).

Data on the effects of parasitic infection on the amount of AM-BP in calf plasma were statistically analyzed using an analysis of variance approach based on the general linear models procedure of SAS (SAS 1986 General Linear Models Procedure: SAS for personal computers, SAS Institute, Cary, N.C.).

Autoradiograms of proteins transferred to nitrocellulose and probed with radiolabeled $^{125}$I-hAM demonstrated that plasma from all of the species tested contained at least one protein that bound to the AM tracer, i.e., an AM-binding protein. This AM-BP was a high molecular weight protein of about 120-130 kD, more specifically, 120 kD. In plasma from the calf, goat, sheep, and to a lesser extent dog, an additional band of 140 kD was observed.

Figure 18:
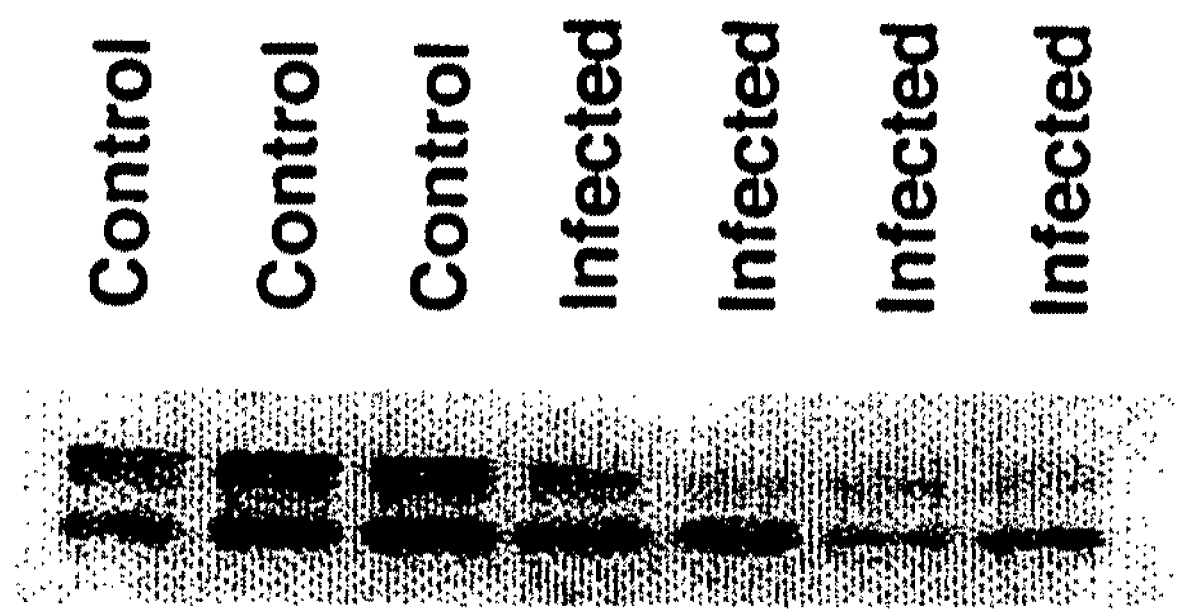
FIG. 18 illustrates decreased levels of AM-binding proteins observed in the plasma of parasitized calves as compared to the plasma of healthy calves. The mean intensity of the bands was decreased by 67% (P<0.03).

In addition, $^{125}$I-AM ligand blotting demonstrated that the content of specific AM-binding proteins was decreased by as much as 68% in plasma of calves experiencing the acute phase response to a parasitic challenge (P<0.03). Because both healthy and parasitized calves had similar plasma concentrations of total proteins, albumin and globulins, the measured decrease in AM-BPs in the parasitized calves reflects a specific response in this protein class to the onset of disease. FIG. 18.

Example 18

A small molecule combinatorial library can be obtained from the Developmental Therapeutics Program at NIH. This library provides a total of 250,000 compounds that have a molecular weight below than $M_r$ 600. The compounds are organized in 8,000 "families" with similar structural characteristics. One member of each family can be assayed for binding to AM, factor H, or AM/fH. If binding is detected, the remaining family members can be analyzed to identify compounds with increased binding affinity for AM, factor H, or AM/fH. In the initial screen, 96-well plates can be coated with AM, factor H, or AM/fH (synthetic, recombinant, or isolated), and then incubated with various test compounds. After extensive washing, the presence of AM, factor H, or AM/fH detected with corresponding antibodies, followed by a secondary antibody and $^{125}$I-protein A. Following this, individual wells can be scanned with a gamma counter. Wells containing AM-, factor H- or AM/fH-binding compounds can be identified by an increase in signal compared the negative control (no compound added).

Compounds that are identified by their binding activity can be further analyzed using various bioassays. For example, compounds can be tested using the fibroblast cell line, Rat-2, which expresses specific AM receptors (H. A. Coppock et al., 1999, *Biochem. J.* 338:15-22.). To test AM-binding compounds, the cells can be incubated with AM alone (negative control) or AM plus the compound. To test fH-binding compounds, the cells can be incubated with AM alone, factor H alone, AM plus factor H (negative controls), or AM plus factor H and the compound. To test AM/fH-binding compounds, the cells can be incubated with AM/fH alone (negative control) or AM/fH plus the compound. Following this, the cAMP response of the cells can be analyzed by radioimmunoassay as previously described (A. Martínez et al., 1997, Endocrinology 138:55977-56048; M. J. Miller et al., 1996, *J. Biol. Chem.* 271:23345-23351; A. Martínez et al., 1999, *Peptides* 20:1471-1478).

Dose-response curves can be plotted and used to identify compounds that inhibit AM-mediated CAMP production (compared to the negative control(s)). The curves can also be used to identify high-affinity compounds. High-affinity compounds can then be used as models for secondary combinatorial libraries that can include ~500 compounds. Such libraries can be assembled from chemically modified forms of the original compound. These new compounds can be tested in the same manner described above to refine the screening process and identify a potent inhibitor of AM function, factor H function, or AM/fH interaction.

All patent applications, patents, texts, and literature references cited in this specification are hereby incorporated herein by reference in their entirety to more fully describe the state of the art to which the present invention pertains.

As various changes can be made in the above methods and compositions without departing from the scope and spirit of the invention as described, it is intended that all subject matter contained in the above description, shown in the accompanying drawings, or defined in the appended claims be interpreted as illustrative, and not in a limiting sense.

We claim:

1. A method for monitoring adrenomedullin concentrations in a subject, comprising:
   incubating a sample from the subject with isolated factor H, or an adrenomedullin-bindable peptide fragment thereof, under conditions allowing binding of factor H or the factor H peptide to adrenomedullin in the sample;
   quantifying the amount of adrenomedullin bound to the factor H or the factor H peptide; and
   comparing the level of adrenomedullin in the subject with level of adrenomedullin in a control.

2. The method according to claim 1, wherein the monitoring of adrenomedullin concentration assists in diagnosing a condition, determining the severity of a condition, or following the recovery course of a condition, wherein the condition is associated with elevated levels of adrenomedullin.

3. The method according to claim 1, wherein the factor H or the factor H peptide comprises a label.

4. The method according to claim 3, wherein the label is non-radioactive or an enzyme.

5. The method according to claim 1, wherein prior to incubating the sample, the sample is fractionated to obtain a peptide fraction sample.

6. The method according to claim 5, wherein the sample is fractionated using a C18 matrix.

7. The method of claim 1, wherein the subject has a condition selected from the group consisting of heart disease, pulmonary disease, liver cirrhosis, cancer, diabetes, sepsis, and inflammation.

8. The method of claim 2, wherein the condition is selected from the group consisting of heart disease, pulmonary disease, liver cirrhosis, cancer, diabetes, sepsis, and inflammation.

* * * * *

UNITED STATES PATENT AND TRADEMARK OFFICE
CERTIFICATE OF CORRECTION

PATENT NO. : 7,659,081 B2
APPLICATION NO. : 12/236418
DATED : February 9, 2010
INVENTOR(S) : Cuttitta et al.

It is certified that error appears in the above-identified patent and that said Letters Patent is hereby corrected as shown below:

On the Title Page

In the Abstract Item (57):

Lines 12-15 of Abstract, "with this complexes." should read --with these complexes.--.

Column 2, lines 3-4, "peripheral vasodilatation has" should read --peripheral vasodilation has--.

Column 2, line 20, "cells increases in" should read --cells increase in--.

Column 6, lines 49-50, "indicates bronchiolaolveolar carcinoma" should read --indicates bronchioalveolar carcinoma--.

Column 7, line 23, "Incubated of" should read --Incubation of--.

Column 7, line 25, "cAMP in the (FIG. 16B)." should read --cAMP in the islets (FIG. 16B).--.

Column 10, line 53, "factor 1, and" should read --factor I, and--.

Column 12, line 55, "shown facilitate" should read --shown to facilitate--.

Column 12, lines 66-67, "against p cells" should read --against β cells--.

Column 15, line 40, "Conn.)." should read --Conn.)).--.

Column 16, line 24, "767-773)." should read --767-773.--

Column 19, line 10, "antibodies specifically" should read --antibodies that specifically--.

Column 19, line 32, "can be also" should read --can also--.

Column 20, line 19, "and effect a" should read --and affect a--.

Column 22, line 47, "15 mm with" should read --15 min with--.

Column 22, line 61, "Carpenteira)" should read --Carpinteria)--.

Signed and Sealed this
Twenty-first Day of June, 2011

David J. Kappos
*Director of the United States Patent and Trademark Office*

Page 1 of 2

CERTIFICATE OF CORRECTION (continued)
U.S. Pat. No. 7,659,081 B2

Column 23, line 32, "SYSTEM®" should read --SYSTEM GOLD®--.

Column 23, line 40, "60 mm." should read --60 min.--.

Column 23, line 49, "electophoresed" should read --electrophoresed--.

Column 25, line 2, "5μm BASIC®" should read --5μm BETA BASIC®--.

Column 25, line 8, "60 mm." should read --60 min.--.

Column 26, line 31, "30 mm." should read --30 min.--.

Column 26, line 56, "10 mm" should read --10 min--.

Column 26, line 62, "RIA) 54.3. ±8.6 pg/ml" should read --RIA) and 54.3 ±8.6 pg/ml--.

Column 28, line 23, "Mich.)." should read --MO).--.

Column 28, line 34, "ULTARLINK®" should read --ULTRALINK®--.

Column 29, line 45, "polyrnerase" should read --polymerase--.

Column 30, line 5, "secretagoges" should read --secretagogues--.

Column 32, line 12, "below than $M_r$." should read --below $M_r$--.

Column 32, line 26, "compared the" should read --compared to the--.

Column 32, line 47, "CAMP" should read --cAMP--.